(12) United States Patent
Naehrig et al.

(10) Patent No.: US 9,524,392 B2
(45) Date of Patent: Dec. 20, 2016

(54) ENCRYPTING GENOMIC DATA FOR STORAGE AND GENOMIC COMPUTATIONS

(71) Applicant: Microsoft Corporation, Redmond, WA (US)

(72) Inventors: Michael Naehrig, Sammamish, WA (US); Kristin Lauter, Redmond, WA (US); Adriana Lopez-Alt, New York, NY (US)

(73) Assignee: MICROSOFT TECHNOLOGY LICENSING, LLC, Redmond, WA (US)

(*) Notice: Subject to any disclaimer, the term of this patent is extended or adjusted under 35 U.S.C. 154(b) by 482 days.

(21) Appl. No.: 14/093,427

(22) Filed: Nov. 30, 2013

(65) Prior Publication Data

US 2015/0154406 A1 Jun. 4, 2015

(51) Int. Cl.
*G06F 21/00* (2013.01)
*H04L 9/00* (2006.01)
*G06F 21/60* (2013.01)
*G06F 19/28* (2011.01)

(52) U.S. Cl.
CPC .......... *G06F 21/602* (2013.01); *G06F 19/28* (2013.01)

(58) Field of Classification Search
CPC .................................................. G06F 21/602
USPC ............................................................ 380/28
See application file for complete search history.

(56) References Cited

U.S. PATENT DOCUMENTS

| 2004/0143403 A1* | 7/2004 | Brandon | G06F 19/28 |
| | | | 702/19 |
| 2012/0201378 A1* | 8/2012 | Nabeel | H04L 9/008 |
| | | | 380/255 |
| 2013/0097417 A1 | 4/2013 | Lauter et al. | |

FOREIGN PATENT DOCUMENTS

| WO | 2012158621 A1 | 11/2012 |
| WO | 2013067542 A1 | 5/2013 |

OTHER PUBLICATIONS

NPL—Yasuda, "Secure Pattern Matching using Homomorphic Encryption" Cloud Computing Workshop—Nov. 8, 2013.*
Ayday, et al., "Privacy-Preserving Computation of Disease Risk by Using Genomic, Clinical, and Environmental Data", In USENIX Security Workshop on Health Information Technologies, Aug. 2013, 10 pages.
Ayday, et al., "Privacy-Enhancing Technologies for Medical Tests Using Genomic Data", In 20th Annual Network & Distributed System Security Symposium, Feb. 2013, 3 pages.
(Continued)

*Primary Examiner* — Longbit Chai
(74) *Attorney, Agent, or Firm* — Aneesh Ashish Mehta; Katherine J. Drakos; Micky Minhas

(57) ABSTRACT

Genomic data encryption embodiments are presented which generally maintain the privacy of genomic data via an encryption scheme which allows computations to be performed on the encrypted data without the need for decryption. The genomic data is encrypted using a homomorphic polynomial encryption scheme to produce a vector of ciphertexts, where each ciphertext represents a different sample of the genomic data and takes the form of a polynomial and its associated coefficients. Computations on the encrypted genomic data are then performed on the vector or vectors of ciphertexts without decrypting the data. The results of the computations are then provided to an end user who decrypts them.

18 Claims, 6 Drawing Sheets

(56) References Cited

OTHER PUBLICATIONS

Boneh, et al., "Private Database Queries Using Somewhat Homomorphic Encryption", In Applied Cryptography and Network Security, Jun. 25, 2013, 21 pages.
Clarke, et al., "Basic Statistical Analysis in Genetic Case-Control Studies", In Nature Protocols, vol. 6, Feb. 3, 2011, 18 pages.
Furihata, et al., "Test of Association between Haplotypes and Phenotypes in Case-Control Studies: Examination of Validity of the Application of an Algorithm for Samples from Cohort or Clinical Trials to Case-Control Samples Using Simulated and Real Data", In Genetics, vol. 174, Issue 3, Nov. 2006, 13 pages.
"International Search Report and Written Opinion Issued in PCT Patent Application No. PCT/US2014/066992", Mar. 10, 2015, 13 Pages.
Lauter, et al., "Private Computation on Encrypted Genomic Data", In Proceedings of Privacy Enhancing Technologies Symposium, Workshop on Genome Privacy, Jul. 29, 2014, 21 Pages.
Lauter, et al., "Can Homomorphic Encryption be Practical?", In Proceedings of the Workshop on Cloud Computing Security Workshop, Oct. 21, 2011, pp. 113-124.
Yasuda, et al., "Secure Pattern Matching using Somewhat Homomorphic Encryption", In Proceedings of the Workshop on Cloud Computing Security Workshop, Nov. 8, 2013, pp. 65-76.

\* cited by examiner

|  | AA | Aa | aa | Sum |
|---|---|---|---|---|
| Controls | $N_{11}$ | $N_{12}$ | $N_{13}$ | $R_1$ |
| Cases | $N_{21}$ | $N_{22}$ | $N_{23}$ | $R_2$ |
| Sum | $C_1$ | $C_2$ | $C_3$ | $N$ |

ENCRYPTING GENOMIC DATA FOR STORAGE AND GENOMIC COMPUTATIONS

BACKGROUND

The development of cloud storage and services has allowed users to offload both storage of their data and associated computations on that data. As a result, businesses can choose to forego the expensive proposition of maintaining their own data centers, relying instead on cloud storage and computational services.

One type of data amenable to cloud storage and computational services is genomic data. The field of genomics involves analyzing the function and structure of genomes. This includes DNA sequencing and genetic mapping, as well as the study of interactions between loci and alleles within the genome. Human genomic data can be mined to identify variants in genes that can contribute to diseases. However, a large and diverse genomic data set is needed to identify these genetic links. To this end large databases of genomic data are being established.

SUMMARY

Genomic data encryption embodiments described herein generally maintain the privacy of genomic data via an encryption scheme which allows computations to be performed on the encrypted data without the need for decryption.

In one embodiment, the genomic data is first encoded as polynomials in a message space of a homomorphic encryption scheme. Then the encoded genomic data is encrypted using the homomorphic polynomial encryption scheme to produce a vector of ciphertexts, where each ciphertext represents a different sample of the genomic data and takes the form of a polynomial and its associated coefficients. The aforementioned computations on the encrypted genomic data are then performed on the vector or vectors of ciphertexts without decrypting the data.

With regard to the aforementioned encoding of the genomic data, in one embodiment this involves, for each real number making up the data, encoding the number by generating a bit decomposition of the number, converting the bit decomposition to a truncated bit decomposition $\vec{\alpha} = (\alpha_k, \ldots, \alpha_0, \alpha_{-1}, \ldots, \alpha_{-u})$ based on the desired precision u, and then encoding the real number as a polynomial using $$e_\alpha(x) \stackrel{def}{=} \sum_{i=0}^{k+u} \beta_i x^i \in R_2,$$

where $\beta_i = \alpha_{i-u}$ and k+u is the total number of bits in the truncated bit decomposition. The encoded real number is then encrypted using an appropriate homomorphic encryption scheme. Computations can then be performed on the encrypted real number data without decryption to produce an encrypted result. In one embodiment, this involves computing on the encrypted real number data using an equation in the form of $G(e_\alpha) = \sum_{i=0}^{D} a_i x^{(D-i)u} \cdot e_\alpha^i$, where D is the degree of the polynomial and the $a_i$'s are prescribed coefficients. The encrypted result can be decrypted using the appropriate homomorphic decryption. Then, the decrypted results are transformed using $$F(\tilde{\alpha}) = \frac{G(e_\alpha)(\bmod(x-2))}{2^{Du}},$$

and evaluated at x=2 to obtain $\tilde{\alpha}$, which represents the truncated real number representing the results.

The foregoing encrypting, computations and decrypting can be accomplished by separate entities. For example, a user can encrypt the data and transmit it for storage in the cloud. In addition, while in the cloud, computations can be performed on the encrypted data, without decryption. The results of these computations can then be provided to an end user (who can be the encrypting user) in encrypted form. The end user then decrypts the results.

It should also be noted that this Summary is provided to introduce a selection of concepts, in a simplified form, that are further described below in the Detailed Description. This Summary is not intended to identify key features or essential features of the claimed subject matter, nor is it intended to be used as an aid in determining the scope of the claimed subject matter.

DESCRIPTION OF THE DRAWINGS

The specific features, aspects, and advantages of the disclosure will become better understood with regard to the following description, appended claims, and accompanying drawings where:

DETAILED DESCRIPTION

Figure 1:
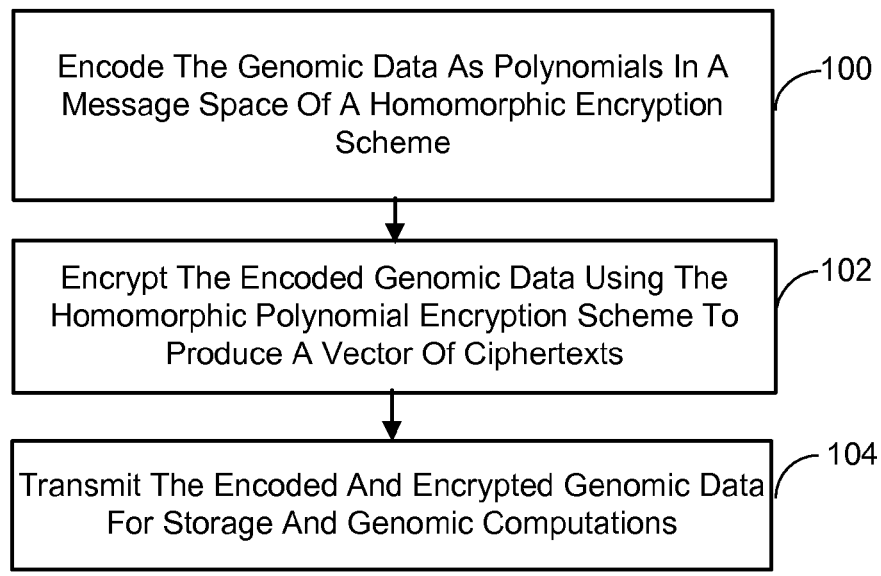
FIG. 1 is a flow diagram generally outlining one embodiment of a process for genomic data encryption.

In the following description of genomic data encryption embodiments reference is made to the accompanying drawings which form a part hereof, and in which are shown, by way of illustration, specific embodiments in which the technique may be practiced. It is understood that other embodiments may be utilized and structural changes may be made without departing from the scope of the technique.

It is also noted that for the sake of clarity specific terminology will be resorted to in describing the genomic data encryption embodiments described herein and it is not intended for these embodiments to be limited to the specific terms so chosen. Furthermore, it is to be understood that each specific term includes all its technical equivalents that operate in a broadly similar manner to achieve a similar purpose. Reference herein to "one embodiment", or "another embodiment", or an "exemplary embodiment", or an "alternate embodiment", or "one implementation", or "another implementation", or an "exemplary implementation", or an "alternate implementation" means that a particular feature, a particular structure, or particular characteristics described in connection with the embodiment or implementation can be included in at least one embodiment of the genomic data encryption. The appearances of the phrases "in one embodiment", "in another embodiment", "in an exemplary embodiment", "in an alternate embodiment", "in one implementation", "in another implementation", "in an exemplary implementation", "in an alternate implementation" in various places in the specification are not necessarily all referring to the same embodiment or implementation, nor are separate or alternative embodiments/implementations mutually exclusive of other embodiments/implementations. Yet further, the order of process flow representing one or more embodiments or implementations of the genomic data encryption does not inherently indicate any particular order nor imply any limitations.

1.0 Genomic Data Encryption

In genetics, a locus is the specific location of a gene or DNA sequence or position on a chromosome. A variant of the similar DNA sequence located at a given locus is called an allele. A single-nucleotide polymorphism (SNP) is a DNA sequence variation occurring when a single nucleotide in the genome (or other shared sequence) differs between members of a biological species or paired chromosomes in a human. In this case it is said that there are two alleles. Chromosomes having the same allele of a given gene at some locus are called homozygous with respect to that gene, while those that have different alleles of a given gene at a locus, are called heterozygous with respect to that gene.

It is advantageous to protect the privacy of individuals who donate their DNA to research, or patients undergoing genomic studies. This is particularly important for cloud storage of the genomic data and cloud-based computations performed using the stored data. These cloud-based computations take individuals' genomic data as input, which potentially compromises patient privacy, even in de-identified data sets. This is because it is possible to find the identity of a person using genomic data and publicly available records. Accordingly, many cloud storage solutions employ encryption on the user's data to preserve data privacy. Unfortunately, it is difficult to efficiently perform meaningful computations on encrypted data without decrypting the data first. The genomic data encryption embodiments described herein protect the privacy of individuals' genomic data while allowing these computational studies to be conducted without decryption.

More particularly the genomic data encryption embodiments described herein employ homomorphic encryption to encrypt encoded genomic data and then to compute on the encrypted data. To this end, referring to FIG. 1, in one embodiment genomic data is first encoded as polynomials in a message space of a homomorphic encryption scheme (process action 100). The encoded genomic data is then encrypted using the homomorphic polynomial encryption scheme to produce a vector of ciphertexts (process action 102). Generally the term "ciphertext" refers to an encrypted data set (e.g., an encrypted message, an encrypted data bit, encrypted text, etc.). In the context of the genomic data encryption embodiments described herein, the ciphertext refers to encrypted genomic data.

It is noted that each ciphertext in a ciphertext vector represents a different sample of the genomic data (e.g., a discrete sample of the genotype or genotype/phenotype pairing associated with a single-nucleotide polymorphism (SNP)) and takes the form of a polynomial and its associated coefficients. It is further noted that multiple ciphertext vectors can be generated, each of which could represent genomic data associated with a different locus. Once the genomic data is encoded and encrypted, it can be transmitted for storage and genomic computations (process action 104). This transmission can be via a computer network (such as the Internet).

With regard to the foregoing action of encrypting the encoded genomic data using a homomorphic polynomial encryption scheme, generally any appropriate homomorphic polynomial encryption method can be employed for this purpose. For example, in one embodiment, a somewhat homomorphic encryption (SwHE) scheme is employed. This SwHE scheme, represented by the expression SwHE= (SH.Keygen,SH.Enc,SH.Add,SH.Mult,SH.Dec), is associated with a number of parameters:

- the dimension n, which is a power of 2;
- the cyclotomic polynomial $f(x)=x^n+1$;
- the modulus q, which is a prime number such that $q \equiv 1 \pmod{2n}$ (together, n, q, and $f(x)$ define rings $R=Z[x]/\langle f(x) \rangle$ and $R_q=R/qR$);
- the error parameter σ, which defines a discrete Gaussian error distribution $\chi=D_{Z^n,\sigma}$ with a standard deviation σ;
- a prime number t<q, which defines the message space of the scheme as $R_t=R/tR$, the ring of integer polynomials modulo $f(x)$ and t; and
- a number D>0, which defines a bound on the maximum number of multiplications that can be performed correctly using the scheme.

In one embodiment, the SwHE scheme is a function of the following component operations:

SH.Keygen($1^K$): a key generation operation, which in one implementation includes (1) sampling a ring element s←χ, (2) defining a secret key sk=s, (3) sampling a uniformly random ring element $a_1 \leftarrow R_q$ and an error e←χ, and (4) computing a public key pk=($a_0$=−($a_1$s+ te), $a_1$);

SH.Enc(pk,m): an encoding operation, which in one implementation includes: (1) encoding the message m as a degree n polynomial with coefficients in $Z_t$—given the public key pk=($a_0,a_1$) and a message m∈$R_q$, the encryption algorithm samples u←χ and f,g←χ, and (2) computing the ciphertext ct=($c_0,c_1$)=($a_0$u+tg+m,$a_1$u+ tf); and SH.Dec(sk, ct=($c_0$, $c_1$, ..., $c_\delta$)): a decryption operation, which in one implementation includes: (1) decrypting by computing $$\tilde{m} = \sum_{i=0}^{\delta} c_i s^i \in R_q,$$

and (2) outputting the message as $\tilde{m}$(mod t).

In addition, the SwHE scheme includes homomorphic operations SH.Add and SH.Mult. In one embodiment, in order to homomorphically compute an arbitrary function $f$, an arithmetic circuit for $f$ (made of addition and multiplication operations over $Z_t$) may be constructed. The SH.Add and SH.Mult operations are used to iteratively compute $f$ on encrypted inputs. Although the ciphertexts produced by SH.Enc contain two ring elements, the homomorphic operations increase the number of ring elements in the ciphertext. In general, the SH.Add and the SH.Mult operations get as input two ciphertexts ct=($c_0$, $c_1$, ..., $c_\delta$) and ct'=($c_0'$, $c_1'$, ..., $c_\gamma'$). The output of SH.Add contains max($\delta$+1, $\gamma$+1) ring elements, whereas the output of SH.Mult contains $\delta$+$\gamma$+1 ring elements.

SH.Add(pk, $ct_0$, $ct_1$): Let ct=($c_0$, $c_1$, ..., $c_\delta$) and ct'=($c_0'$, $c_1'$, ..., $c_\gamma'$) be two ciphertexts. Assume that $\delta$=$\gamma$, otherwise, pad the shorter ciphertext with zeroes. Homomorphic addition is accomplished by component-wise addition of the ciphertexts. Namely, compute and output $$ct_{add} = (c_0+c_0', c_1+c_1', \ldots, c_{max(\delta,\gamma)}+c'_{max(\delta,\gamma)}) \in R_q^{max(\delta,\gamma)}$$

SH.Mult(pk, $ct_0$, $ct_1$): Let ct=($c_0$, $c_1$, ..., $c_\delta$) and ct'=($c_0'$, $c_1'$, ..., $c_\gamma'$) be two ciphertexts. Let v be a symbolic variable and consider the expression $$\left(\sum_{i=0}^{\delta} c_i v^i\right) \cdot \left(\sum_{i=0}^{\gamma} c_i' v^i\right) \text{ over } R_q, \quad (1)$$

Eq. (1) can be decomposed by symbolically treating v as an unknown variable to compute $\hat{c}_0, \ldots, \hat{c}_{\delta+\lambda} \in R_q$ such that for all $v \in R_q$ $$\left(\sum_{i=0}^{\delta} c_i v^i\right) \cdot \left(\sum_{i=0}^{\gamma} c_i' v^i\right) \equiv \sum_{i=0}^{\delta+\gamma} \hat{c}_i v^i \quad (2)$$

The output ciphertext is $ct_{mult}$=($\hat{c}_0$, ..., $\hat{c}_{\delta+\gamma}$).

With regard to the foregoing action of transmitting the encoded and encrypted genomic data for storage and genomic computations, this can involve sending the data to cloud storage and performing the computations in the cloud as well. In this context, being "in the cloud" refers to computing concepts involving a large number of computers connected through a real-time computer network (such as the Internet). The encoded and encrypted data can be stored on one or more of these computers, and the aforementioned computations can be perform on one or more of these computers as well (either the same computer or computers, a different computer or computers, or any combination thereof).

Figure 2:
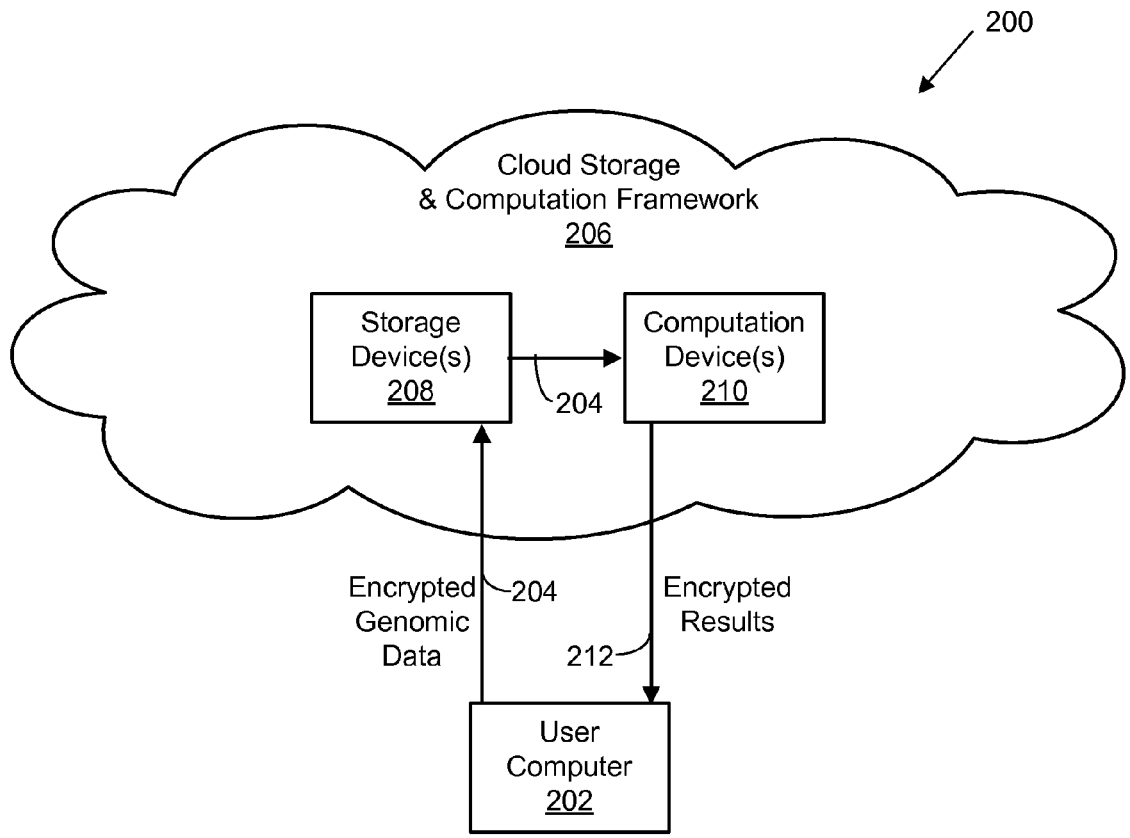
FIG. 2 depicts a simplified diagram of a computing environment for receiving encoded and encrypted genomic data from a user, storing the encrypted data, performing computations on the data without decrypting it first, and providing the results of the computations in the same encrypted form to the user.

FIG. 2 illustrates an example of the foregoing computing environment 200 for receiving encoded and encrypted genomic data from a user, storing the encrypted data, performing computations on the data without decrypting it first, and providing the results of the computations in the same encrypted form to the user. The user, as represented in the FIG. 2 by the user computer 202 (which is in communication with a computer network such as the Internet), encodes and encrypts the genomic data as described previously. This encrypted data 204 is transmitted via the computer network to a cloud storage and computation framework 206 (which can be one or more computers also in communication with the computer network). The encrypted genomic data 204 is received by one or more storage devices 208 residing within the cloud storage and computation framework 206. The aforementioned genomic computations are then performed on the encrypted data 204. In the depicted example one or more computation devices 210 residing within the cloud storage and computation system 206 obtain the stored encrypted data 204 from the storage device or devices 208 and perform the genomic computations without decrypting the data. The computation device or devices 210 then transmit the results of the genomic computations 212 to an end user. In the depicted example, the end user is the user computer 202 (although this need not be the case). It is noted that the results exhibit the same encryption as the genomic data. It is further noted that in other embodiments, the storage device or devices could also perform the computations and so act as the one or more computation devices.

Figure 3:
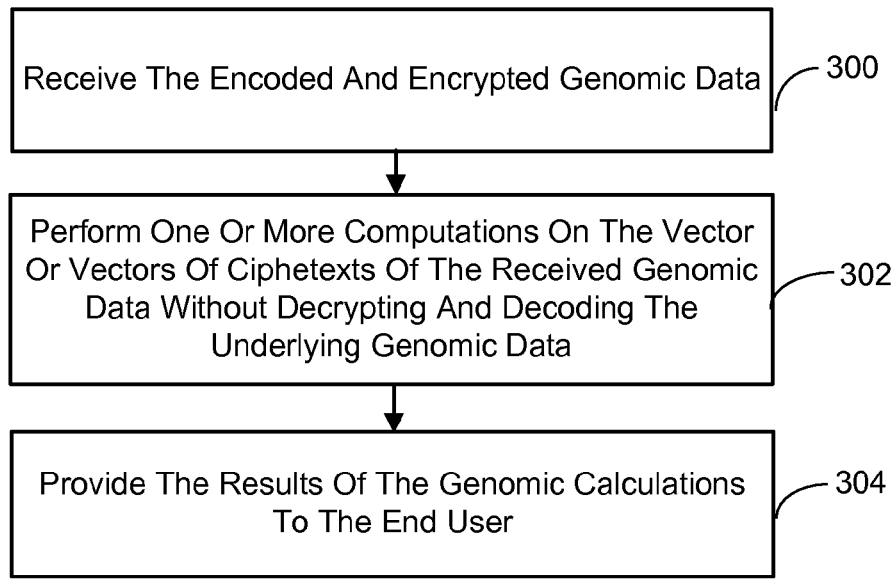
FIG. 3 is a flow diagram generally outlining one embodiment of a process for performing genomic computations on encoded and encrypted genomic data without decrypting the data.

Referring now to FIG. 3, an exemplary process for performing the aforementioned genomic computations is outlined. First, one or more computers (e.g., in the cloud) receive the encoded and encrypted genomic data (process action 300). As indicated previously this data includes at least one vector of ciphertexts, each ciphertext of which represents a different sample of the genomic data and takes the form of a polynomial and its associated coefficients. One or more computations are performed on the vector or vectors of ciphertexts without having to decrypt and decode the underlying genomic data (process action 302). These genomic computations correspond to statistical analyses that have been developed by computational biologists and statisticians to conduct genomic correlation studies on genomic data in populations. For example, as will be described in greater detail later, some of the genomic computations possible include the Pearson Goodness-of-Fit (Chi-Squared) Test to measure data quality, the Cochran-Armitage Test for trends on the correlations between genotypes and phenotypes, Estimation Maximization Algorithm for Haplotyping to estimate haplotype frequencies from genotype counts, and Linkage Disequilibrium statistic to estimate correlation between genes. These types of genomic computations involve multiplication and addition of the ciphertext vector(s).

Once the foregoing genomic calculations are complete, the results are provided to an end user (process action 304). It is noted that the end user can be the same entity that encoded and encrypted the genomic data in the first place (as shown in FIG. 2), or a different party that is authorized by the encoding and encrypting party to decrypt and decode the results. The results can be provided via a transmission over a computer network (such as the Internet).

1.1 Encoding and Encrypting Genotypes

For a plaintext m, the encryption of m is denoted as $\hat{m}$. For a single SNP, there are 3 possible genotypes which are represented as 0,1,2 with 1 being the heterozygous genotype and 0,2 being the homozygous genotypes. Additionally, there may be a missing genotype which is represented as −9.

The genotype numbers are encoded as elements in the ring $$R_q \stackrel{def}{=} R/qR$$

where $$R \stackrel{def}{=} Z[x]/\langle x^n + 1 \rangle$$

(as described previously), and this encoding can be arbitrarily chosen as $E_g: \{0,1,2,-9\} \to R_q$. To ensure that the coefficients of the encoding (in $R_q$) are small, the following further encoding is employed:

$$E_g(z) \stackrel{def}{=} \begin{cases} -1 & z = 0 \\ 0 & z = 1 \\ 1 & z = 2 \\ x^\tau & z = -9 \end{cases} \quad (3)$$

where $\tau \stackrel{def}{=} \log t$

Note that $t=2^\tau$ is defined to be a power of 2.

Next, an indicator function $g_i$ is defined by:

$$g_i(z) = \begin{cases} 1 & z = E_g(i) \\ 0 & z \neq E_g(i) \end{cases} \quad (4)$$

The input is a vector $$\vec{z} \stackrel{def}{=} (z_1, \ldots, z_k)^T \in \{-1, 0, 1, x^\tau\}$$

of genotype samples. Let $(2^{-1})_q$ denote the inverse of 2 modulo q. Lagrange interpolation can be employed to find the polynomial computing each $g_i$. In one implementation, the following polynomials are computed (over $R_q$):

$$g_0(z) \stackrel{def}{=} (2^{-1})_q \cdot (z^2 - z), \; g_1(z) \stackrel{def}{=} (1-z^2)(1+z \cdot x^{n-\tau}), \quad (5)$$

$$g_2(z) \stackrel{def}{=} (2^{-1})_q \cdot (z^2 + z)$$

As a sanity check, note that for $z \in \{-1,0,1\}$, $g_i(z)=1$ if $z=E(i)$ and $g_i(z)=0$ if $z \neq E(i)$. When $z=-9$, it is desired that $g_i(z)=0$ always. This is not achieved exactly, but instead the functionally equivalent values are:

$$g_0(x^\tau)=(2^{-1})_q \cdot (x^{2\tau}-x^\tau), g_1(x^\tau)=(1-x^{2\tau})(1+x^n)=0, g_2(x^\tau)= (2^{-1})_q \cdot (x^{2\tau}+x^\tau) \quad (6)$$

Note that $g_1(x^\tau)=0$ because $1+x^n=0$ in $R_q$. The case for $g_0$ and $g_2$ is different, but functionally equivalent because at decoding these polynomials will evaluate to 0. More particularly, to decode a polynomial $p(x)$, $p(x)$ mod $t$ is computed where $x=2$ and mod $t=x^\tau$. Accordingly, the encoding for a missing genotype, $x^\tau$, decodes to 0 but its encoding is non-zero, guaranteeing that all encodings are distinct.

Further, as indicted previously, care is taken so that after the entire computation of the algorithm, there is no reduction mod $x^n+1$. This will guarantee that decoding gives the correct output. Therefore, if the algorithm it is desired to compute can be represented as a polynomial of degree D, care is taken to ensure that $2^D \cdot \tau < n$.

Once the polynomials are computed and it has been determined there is no reduction mod $x^n+1$, the encryption can proceed as described previously.

1.1.1 Counting Genotype Frequencies

The first step in certain genomic computations is to compute genotype frequencies. For a specific genotype $i \in \{0,1,2\}$ the total number of samples with genotype i is computed (call it $N_i$) by summing over all samples z. In term of computing genotype frequencies on the now encrypted genomic data, in one embodiment, the following procedure for counting genotypes is employed. The genotype counts represent the aforementioned frequencies.

Given a vector of ciphertexts $(\hat{z}_1, \ldots, \hat{z}_K)$ encrypting genotype samples in $\{-1,0,1,x^\tau\}$, the genotype frequencies are counted using:

$$\hat{N}_0 \leftarrow \Sigma_{k=1}^K g_0(\hat{z}_k), \hat{N}_1 \leftarrow \Sigma_{k=1}^K g_1(\hat{z}_k), \hat{N}_2 \leftarrow \Sigma_{k=1}^K g_2(\hat{z}_k) \quad (7)$$

This produces ciphertexts $\hat{N}_0$, $\hat{N}_1$, $\hat{N}_2$ such that $\deg(\hat{N}_0, \hat{N}_2)=2$ and $\deg(\hat{N}_1)=3$, where $\hat{N}_0$, $\hat{N}_1$, $\hat{N}_2$ represent the encrypted genotype frequencies of the first homozygous genotype (0), the heterozygous genotype (1), and the second homozygous genotype (2), respectively.

Figure 4:
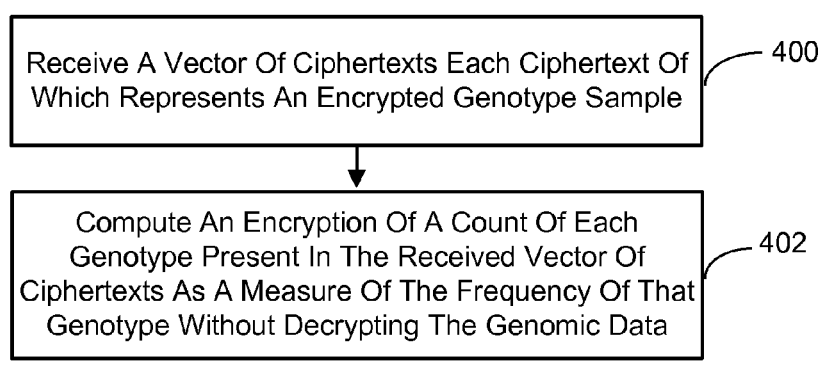
FIG. 4 is a flow diagram generally outlining an implementation of the part of the process of FIG. 3 involving the computation of genotype frequency for a single locus.

In procedural terms, referring to FIG. 4, the foregoing genotype frequency computation involves first receiving a vector of ciphertexts each of which represents an encrypted genotype sample (process action 400). Then, an encryption of a count of each genotype present in the received vector of ciphertexts is computed as a measure of the frequency of that genotype (process 402). It is noted that this last action is performed without decrypting the genomic data.

1.1.2 Genomic Computations Using Encrypted Genotype Frequencies

Once the encrypted genotype frequencies are computed, various genomic computation can be performed using the encrypted data. For example, the aforementioned Pearson Goodness-of-Fit (Chi-Squared) Test, Estimation Maximization Algorithm for Haplotyping and Linkage Disequilibrium computations can be performed, as will be described in more detail in the sections to follow.

It is noted that certain definitions apply to the following descriptions of the genomic computations. For example, the $\chi^2$ distribution with k degrees of freedom is defined as the distribution obtained from adding the squares of k independent standard normal random variables. In addition, the p-value of a test statistic T in comparison to distribution D is defined as the probability according to D of having observed an outcome at least as extreme as the value observed. For test statistics $T>0$, the p-value of T in comparison to D is $\Pr[D \geq T]=1-CDF_D(T)$. For significance level $\alpha$ and p-value p, it is concluded that the deviation of T from D is statistically significant if $p < \alpha$. Common significance levels are 0.05 and 0.01.

1.1.2.1 Pearson Goodness-of-Fit (Chi-Squared) Test

The Pearson Goodness-Of-Fit (Chi-Squared) Test is a test for deviations from Hardy-Weinberg Equilibrium. Hardy-Weinberg Equilibrium (HWE) is a principle that states that allele frequencies will stay the same from generation to generation unless perturbed by evolutionary influences.

Equivalently, the HWE states that allele frequencies are independent. More formally, consider two alleles A and a and let $p_A$, $p_a$ be their corresponding population frequencies, so that $p_a=1-p_A$. Similarly, let $p_{AA}$, $p_{Aa}$, $p_{aa}$ be the corresponding population frequencies for genotypes AA, Aa, aa. Then alleles A and a are independent (and HWE holds) if:

$$p_{AA}=p_A^2, p_{Aa}=2p_Ap_a, p_{aa}=p_a^2. \quad (8)$$

Let $N_{AA}$, $N_{Aa}$, $N_{aa}$ be the observed counts for genotypes AA, Aa, aa, respectively, and let $$N \stackrel{def}{=} N_{AA} + N_{Aa} + N_{aa}$$

be the total number of samples. Then the frequency of alleles A and a can be calculated by:

$$p_A = \frac{2N_{AA} + N_{Aa}}{2N}, \quad p_a = 1 - p_A. \quad (9)$$

Thus, HWE indicates that the following counts are expected:

$$E_{AA} \stackrel{def}{=} Np_A^2, \quad E_{Aa} \stackrel{def}{=} 2Np_Ap_a, \quad E_{aa} \stackrel{def}{=} Np_a^2. \quad (10)$$

Deviation from the HWE is tested by comparing the following test-statistic to the $\chi^2$-statistic with 1 degree of freedom (3 genotypes minus 2 alleles):

$$X^2 \stackrel{def}{=} \sum_{i \in \{AA,Aa,aa\}} \frac{(N_i - E_i)^2}{E_i} \quad (11)$$

To do this, the p-value p of $X^2$ is computed according to the $\chi^2$-distribution with 1 degree of freedom. It is then concluded that the data is in HWE only if $p>\alpha$, for significance level $\alpha$. When $\alpha=0.05$, this reduces to checking if $X^2<3.84$; and when $\alpha=0.01$, this reduces to checking if $X^2<6.64$.

The expected counts can be computed as:

$$E_0 = N\left(\frac{2N_0 + N_1}{2N}\right)^2, \quad (12)$$

$$E_1 = 2N\left(\frac{2N_0 + N_1}{2N}\right)\left(\frac{2N_2 + N_1}{2N}\right), \quad E_2 = N\left(\frac{2N_2 + N_1}{2N}\right)^2,$$

which can be simplified to:

$$E_0 = \frac{(2N_0 + N_1)^2}{4N}, \quad E_1 = \frac{(2N_0 + N_1)(2N_2 + N_1)}{2N}, \quad E_2 = \frac{(2N_2 + N_1)^2}{4N}. \quad (13)$$

The test statistic $X^2$ can then be computed as:

$$X^2 = \frac{(N_0 - E_0)^2}{E_0} + \frac{(N_1 - E_1)^2}{E_1} + \frac{(N_2 - E_2)^2}{E_2} \quad (14)$$

-continued $$= \frac{(4N_0N_2 - N_1^2)^2}{4N(2N_0 + N_1)^2} + \frac{(4N_0N_2 - N_1^2)^2}{2N(2N_0 + N_1)(2N_2 + N_1)} + \frac{(4N_0N_2 - N_1^2)^2}{4N(2N_2 + N_1)^2}$$

$$= \frac{(4N_0N_2 - N_1^2)^2}{2N}\left(\frac{1}{2(2N_0 + N_1)^2} + \frac{1}{(2N_0 + N_1)(2N_2 + N_1)} + \frac{1}{2(2N_2 + N_1)^2}\right)$$

It therefore suffices to return encryptions of $\alpha$, N, $\beta_1$, $\beta_2$, $\beta_3$, where:

$$\alpha \stackrel{def}{=} (4N_0N_2 - N_1^2)^2, \quad \beta_1 \stackrel{def}{=} 2(2N_0 + N_1)^2, \quad (15)$$

$$\beta_2 \stackrel{def}{=} (2N_0 + N_1)(2N_2 + N_1), \quad \beta_3 \stackrel{def}{=} 2(2N_2 + N_1)^2$$

In view of the foregoing, the Pearson Goodness-Of-Fit (Chi-Squared) Test can be performed using encrypted genotype frequencies as follows. The encrypted genotype frequency counts $\hat{N}_0$, $\hat{N}_1$, $\hat{N}_2$ with $\deg(\hat{N}_0,\hat{N}_2)=2$ and $\deg(\hat{N}_1)=3$ generated from the vector of ciphertexts $(\hat{z}_1, \ldots, \hat{z}_K)$ encrypting genotype samples in $\{-1,0,1,x^\tau\}$ are input. Ciphertexts $\hat{\alpha}, \hat{N}, \hat{\beta}_1, \hat{\beta}_2, \hat{\beta}_3$ are then computed as follows:

$$\hat{\alpha} \leftarrow (4\hat{N}_0\hat{N}_2 - \hat{N}_1^2)^2 \text{ where } \deg(\hat{\alpha})=12; \quad (16)$$

$$\hat{N} \leftarrow \hat{N}_0 + \hat{N}_1 + \hat{N}_2 \text{ where } \deg(\hat{N})=3; \text{ and} \quad (17)$$

$$\hat{\beta}_1 \leftarrow 2(2\hat{N}_0 + \hat{N}_1)^2$$

$$\hat{\beta}_2 \leftarrow (2\hat{N}_0 + \hat{N}_1)(2\hat{N}_2 + \hat{N}_1) \text{ where } \deg(\hat{\beta}_i)=6$$

$$\hat{\beta}_3 \leftarrow 2(2\hat{N}_2 + \hat{N}_1)^2. \quad (18)$$

The ciphertexts $\hat{\alpha}, \hat{N}, \hat{\beta}_1, \hat{\beta}_2, \hat{\beta}_3$ are then output (such as to the user as described previously). Once decrypted and decoded, $X^2$ can be computed such that:

$$X^2 = \frac{\alpha}{2N}\left(\frac{1}{\beta_1} + \frac{1}{\beta_2} + \frac{1}{\beta_3}\right). \quad (19)$$

1.1.2.2 Estimation Maximization for Haplotyping

Haplotypes cannot be exactly determined from genotypes. For example, consider two bi-allelic loci with alleles A,a and B,b. The genotype AaBb can be one of two possible haplotypes: (AB)(ab) or (Ab)(aB). Estimation Maximization (EM) is used to estimate haplotype frequencies from genotype counts. The EM procedure is an iterative method to estimate haplotype frequencies, starting with arbitrary initial values $p_{AB}^{(0)}, p_{Ab}^{(0)}, p_{aB}^{(0)}, p_{ab}^{(0)}$. These values are first used in an estimation stage to calculate the expected genotype frequencies (assuming the initial values are the true haplotype frequencies), and these, in turn, are used to estimate the haplotype frequencies for the next iteration in the maximization stage. The procedure stops when the haplotype frequencies have stabilized.

More particularly, in the ith estimation iteration:

$$E_{AB/ab}^{(i)} \stackrel{def}{=} [N_{AB/ab} \mid N_{AaBb}, p_{AB}^{(0)}, p_{Ab}^{(0)}, p_{aB}^{(0)}, p_{ab}^{(0)}] \quad (20)$$

$$= N_{AaBb} \cdot \frac{p_{AB}^{(i-1)} p_{ab}^{(i-1)}}{p_{AB}^{(i-1)} p_{ab}^{(i-1)} + p_{Ab}^{(i-1)} p_{aB}^{(i-1)}}$$

-continued $$E_{Ab/aB}^{(i)} \stackrel{def}{=} \vdash [N_{Ab/aB} \mid N_{AaBb}, p_{AB}^{(0)}, p_{Ab}^{(0)}, p_{aB}^{(0)}, p_{ab}^{(0)}] \quad (21)$$

$$= N_{AaBb} \cdot \frac{p_{Ab}^{(i-1)} p_{aB}^{(i-1)}}{p_{AB}^{(i-1)} p_{ab}^{(i-1)} + p_{Ab}^{(i-1)} p_{aB}^{(i-1)}};$$

and in the ith maximization iteration, $$N_{AB}^{(i)} = 2N_{AABB} + N_{AABb} + N_{AaBB} + E_{AB/ab}^{(i)}$$

$$N_{ab}^{(i)} = 2N_{aabb} + N_{aaBb} + N_{Aabb} + E_{AB/ab}^{(i)}$$

$$N_{Ab}^{(i)} = 2N_{AAbb} + N_{AABb} + N_{Aabb} + E_{Ab/aB}^{(i)}$$

$$N_{aB}^{(i)} = 2N_{aaBB} + N_{AaBB} + N_{aaBb} + E_{Ab/aB}^{(i)} \quad (22)$$

Before running the EM procedure, the 9 genotype counts $N_{ij}$ for $i,j \in \{0,1,2\}$ are computed. This can be done with the function $f_{ij}(z,z')=g_i(z) \cdot g_j(z')$. In terms of the encrypted genotype frequency counts, the foregoing amounts to counting genotype frequencies for two loci.

More particularly, given two vectors of ciphertexts $(\hat{z}_1, \ldots, \hat{z}_K)$, $(\hat{z}'_1, \ldots, \hat{z}'_K)$ encrypting genotype samples in $\{-1,0,1,x^\tau\}$, for loci 1 and 2 respectively, the genotype frequencies for two loci are counted using:

$$\hat{N}_{ij} \leftarrow \Sigma_{k=1}^K g_i(\hat{z}_k) \cdot g_j(\hat{z}'_k) \text{ for } i,j \in \{0,1,2\}. \quad (23)$$

This produces ciphertexts $\hat{N}_{00}, \hat{N}_{10}, \hat{N}_{20}, \hat{N}_{01}, \hat{N}_{11}, \hat{N}_{21}, \hat{N}_{02}, \hat{N}_{12}, \hat{N}_{22}$ such that $\deg(\hat{N}_{ij}) \leq 6$.

Figure 5:
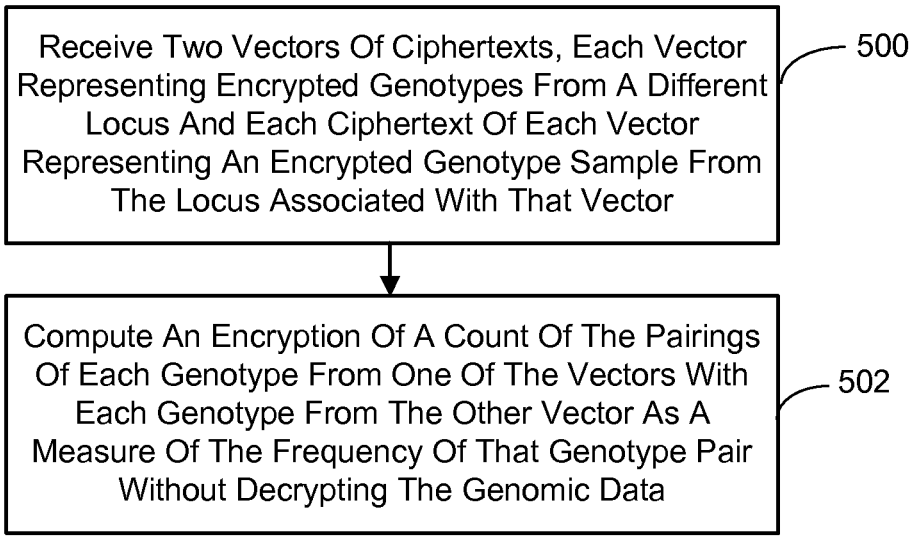
FIG. 5 is a flow diagram generally outlining an implementation of the part of the process of FIG. 3 involving the computation of genotype pair frequency for two loci.

In procedural terms, referring to FIG. 5, the foregoing frequency computation for two loci involves first receiving two vectors of ciphertexts, each vector representing encrypted genotypes from a different locus and each ciphertext of each vector representing an encrypted genotype sample from the locus associated with that vector (process action 500). Then, an encryption of a count of the pairings of each genotype from one of the vectors with each genotype from the other vector is computed as a measure of the frequency of that genotype pair (process 502). It is noted that this last action is performed without decrypting the genomic data.

Referring again to performing the EM procedure, the estimated haplotype frequencies $p_*^{(i)}$ are real numbers. These can be substituted by the estimated haplotype counts $$N_*^{(i)} \stackrel{def}{=} 2N \cdot p_*^{(i)}$$

since this does not change the fraction in $\mu_{AB/ab}^{(i)}$ and $\mu_{Ab/aB}^{(i)}$ (essentially, this change multiplies both the numerator and the denominator by $4N^2$). This modifies the ith estimation iteration as follows:

$$E_{AB/ab}^{(i)} = N_{11} \cdot \frac{N_{AB}^{(i-1)} N_{ab}^{(i-1)}}{N_{AB}^{(i-1)} N_{ab}^{(i-1)} + N_{Ab}^{(i-1)} N_{aB}^{(i-1)}} \stackrel{def}{=} \frac{\alpha^{(i)}}{\beta^{(i)}}; \quad (24)$$

$$E_{Ab/aB}^{(i)} = N_{11} \cdot \frac{N_{Ab}^{(i-1)} N_{aB}^{(i-1)}}{N_{AB}^{(i-1)} N_{ab}^{(i-1)} + N_{Ab}^{(i-1)} N_{aB}^{(i-1)}} \stackrel{def}{=} \frac{\gamma^{(i)}}{\beta^{(i)}}. \quad (25)$$

It is also possible to simplify each iteration so that at any given point, only one numerator and one denominator are needed by defining:

$$\zeta_{AB} \stackrel{def}{=} 2N_{22} + N_{21} + N_{12}; \quad (26)$$

$$\zeta_{ab} \stackrel{def}{=} 2N_{00} + N_{01} + N_{10};$$

$$\zeta_{Ab} \stackrel{def}{=} 2N_{20} + N_{21} + N_{10};$$

$$\zeta_{aB} \stackrel{def}{=} 2N_{02} + N_{12} + N_{01}.$$

Then:

$$N_{AB}^{(i)} = \zeta_{AB} + E_{AB/ab}^{(i)} = \zeta_{AB} + \frac{\alpha^{(i)}}{\beta^{(i)}} = \frac{\zeta_{AB} \cdot \beta^{(i)} + \alpha^{(i)}}{\beta^{(i)}}; \quad (27)$$

$$N_{ab}^{(i)} = \zeta_{ab} + E_{AB/ab}^{(i)} = \zeta_{ab} + \frac{\alpha^{(i)}}{\beta^{(i)}} = \frac{\zeta_{ab} \cdot \beta^{(i)} + \alpha^{(i)}}{\beta^{(i)}}; \quad (28)$$

$$N_{Ab}^{(i)} = \zeta_{Ab} + E_{Ab/aB}^{(i)} = \zeta_{Ab} + \frac{\gamma^{(i)}}{\beta^{(i)}} = \frac{\zeta_{Ab} \cdot \beta^{(i)} + \gamma^{(i)}}{\beta^{(i)}}; \quad (29)$$

$$N_{aB}^{(i)} = \zeta_{aB} + E_{Ab/aB}^{(i)} = \zeta_{aB} + \frac{\gamma^{(i)}}{\beta^{(i)}} = \frac{\zeta_{aB} \cdot \beta^{(i)} + \gamma^{(i)}}{\beta^{(i)}}. \quad (30)$$

At the next estimation iteration (i+1)th, the following is computed:

$$E_{AB/ab}^{(i+1)} = N_{11} \cdot \frac{\left(\frac{\zeta_{AB} \cdot \beta^{(i)} + \alpha^{(i)}}{\beta^{(i)}}\right)\left(\frac{\zeta_{ab} \cdot \beta^{(i)} + \alpha^{(i)}}{\beta^{(i)}}\right)}{\left(\frac{\zeta_{AB} \cdot \beta^{(i)} + \alpha^{(i)}}{\beta^{(i)}}\right)\left(\frac{\zeta_{ab} \cdot \beta^{(i)} + \alpha^{(i)}}{\beta^{(i)}}\right) + \left(\frac{\zeta_{Ab} \cdot \beta^{(i)} + \gamma^{(i)}}{\beta^{(i)}}\right)\left(\frac{\zeta_{aB} \cdot \beta^{(i)} + \gamma^{(i)}}{\beta^{(i)}}\right)} \quad (31)$$

$$= N_{11} \cdot \frac{(\zeta_{AB} \cdot \beta^{(i)} + \alpha^{(i)})(\zeta_{ab} \cdot \beta^{(i)} + \alpha^{(i)})}{(\zeta_{AB} \cdot \beta^{(i)} + \alpha^{(i)})(\zeta_{ab} \cdot \beta^{(i)} + \alpha^{(i)}) + (\zeta_{Ab} \cdot \beta^{(i)} + \gamma^{(i)})(\zeta_{aB} \cdot \beta^{(i)} + \gamma^{(i)})} \stackrel{def}{=} \frac{\alpha^{(i+1)}}{\beta^{(i+1)}}$$

Similarly, $$E_{Ab/aB}^{(i+1)} = N_{11} \cdot \frac{((\zeta_{Ab} \cdot \beta^{(i)} + \gamma^{(i)})(\zeta_{aB} \cdot \beta^{(i)} + \gamma^{(i)}))}{(\zeta_{AB} \cdot \beta^{(i)} + \alpha^{(i)})(\zeta_{ab} \cdot \beta^{(i)} + \alpha^{(i)}) + (\zeta_{Ab} \cdot \beta^{(i)} + \gamma^{(i)})(\zeta_{aB} \cdot \beta^{(i)} + \gamma^{(i)})} \stackrel{def}{=} \frac{\gamma^{(i+1)}}{\beta^{(i+1)}} \quad (32)$$

In other words, since the denominator, $\beta^{(i)}$, of the $N_*^{(i)}$'s always cancels out, only the numerators need be noted. The numerators depend on $\beta^{(i)}$, so it is still computed as part of the numerator computation, but there is no need to keep track of it after this computation (with the exception that at the last iteration, it is necessary to divide by $\beta^{(i)}$ to maintain correctness).

In view of the foregoing, the ith estimation iteration is, $$\alpha^{(i)} = N_{11} \cdot N_{AB}^{(i-1)} N_{ab}^{(i-1)}; \gamma^{(i)} = N_{11} \cdot N_{Ab}^{(i-1)} N_{aB}^{(i-1)},$$
$$\beta^{(i)} = N_{AB}^{(i-1)} N_{ab}^{(i-1)} + N_{Ab}^{(i-1)} N_{aB}^{(i-1)}, \quad (33)$$

and the ith maximization iteration is, $$N_{AB}^{(i)} = \zeta_{AB} \cdot \beta^{(i)} + \alpha^{(i)}, N_{ab}^{(i)} = \zeta_{ab} \cdot \beta^{(i)} + \alpha^{(i)}, N_{Ab}^{(i)} = \zeta_{Ab} \cdot \beta^{(i)} + \gamma^{(i)}, N_{aB}^{(i)} = \zeta_{aB} \cdot \beta^{(i)} + \gamma^{(i)}. \quad (34)$$

In each iteration, the degree goes from D to 2D+6. Starting with unencrypted estimations $N_*^{(0)}$ (with degree 0), after m iterations the degree is $6 \cdot (2^m - 1)$.

In view of the foregoing, the EM Algorithm for Haplotyping can be performed using encrypted genotype frequencies as follows. The two vectors of ciphertexts $(\hat{z}_1, \ldots, \hat{z}_K)$, $(\hat{z}'_1, \ldots, \hat{z}'_K)$ encrypting genotype samples in $\{-1,0,1,x^\tau\}$, for loci 1 and 2 respectively, and number of iterations m to be performed, are input, along with the ciphertexts $\hat{N}_{00}$, $\hat{N}_{10}$, $\hat{N}_{20}$, $\hat{N}_{01}$, $\hat{N}_{11}$, $\hat{N}_{21}$, $\hat{N}_{02}$, $\hat{N}_{12}$, $\hat{N}_{22}$ computed as described previously. Ciphertexts $\hat{\eta}$, $\hat{\beta}$ are then computed as follows:

$$\hat{\xi}_1 \leftarrow 2\hat{N}_{11} + \hat{N}_{12} + \hat{N}_{21}$$

$$\hat{\xi}_2 \leftarrow 2\hat{N}_{33} + \hat{N}_{32} + \hat{N}_{23} // \deg(\hat{\xi}_i) = 6;$$

$$\hat{\xi}_3 \leftarrow 2\hat{N}_{13} + \hat{N}_{12} + \hat{N}_{23}$$

$$\hat{\xi}_4 \leftarrow 2\hat{N}_{31} + \hat{N}_{21} + \hat{N}_{32} \tag{35}$$

$$\hat{N} \leftarrow \hat{N}_{00} + \hat{N}_{10} + \hat{N}_{20} + \hat{N}_{01} + \hat{N}_{11} + \hat{N}_{21} + \hat{N}_{02} + \hat{N}_{12} + \hat{N}_{22} // \deg(\hat{N}) = 6; \tag{36}$$

$$\hat{\eta}_1^{(0)} \leftarrow \hat{N}, \hat{\eta}_2^{(0)} \leftarrow \hat{N}, \hat{\eta}_3^{(0)} \leftarrow \hat{N}, \hat{\eta}_4^{(0)} \leftarrow \hat{N} // \deg(\hat{\eta}_i^{(0)}) = 6; \tag{37}$$

$$\hat{\beta}^{(0)} \leftarrow 2 // \deg(\hat{\beta}^{(0)}) = 0; \tag{38}$$

For each iteration $i \leftarrow 1$ to m $$\hat{\alpha}^{(i)} \leftarrow \hat{N}_{22} \cdot \hat{\eta}_1^{(i-1)} \hat{\eta}_2^{(i-1)} \tag{39}$$

$$\hat{\gamma}^{(i)} \leftarrow \hat{N}_{22} \cdot \hat{\eta}_3^{(i-1)} \hat{\eta}_4^{(i-1)} // \deg(\hat{\alpha}^{(i)}, \hat{\gamma}^{(i)}) = 6 \cdot (2^i - 1) \tag{40}$$

$$\hat{\beta}^{(i)} \leftarrow \hat{\eta}_1^{(i-1)} \hat{\eta}_2^{(i-1)} + \hat{\eta}_3^{(i-1)} \hat{\eta}_4^{(i-1)} // \deg(\hat{\beta}^{(i)}) = 6 \cdot (2^i - 2) \tag{41}$$

$$\hat{\eta}_1^{(i)} \leftarrow \hat{\xi}_1 \cdot \hat{\beta}^{(i)} + \hat{\alpha}^{(i)}$$

$$\hat{\eta}_2^{(i)} \leftarrow \hat{\xi}_2 \cdot \hat{\beta}^{(i)} + \hat{\alpha}^{(i)} // \deg(\hat{\eta}_j^{(i)}) = 6 \cdot (2^i - 1)$$

$$\hat{\eta}_3^{(i)} \leftarrow \hat{\xi}_3 \cdot \hat{\beta}^{(i)} + \hat{\gamma}^{(i)}$$

$$\hat{\eta}_4^{(i)} \leftarrow \hat{\xi}_4 \cdot \hat{\beta}^{(i)} + \hat{\gamma}^{(i)} \tag{42}$$

$$\hat{\eta} \leftarrow \hat{\eta}_1^{(m)} // \deg(\hat{\eta}) = 6 \cdot (2^m - 1) \tag{43}$$

$$\hat{\beta} \leftarrow \hat{\beta}^{(m)} // \deg(\hat{\beta}) = 6 \cdot (2^m - 2) \tag{44}$$

The ciphertexts $\hat{\eta}, \hat{\beta}$ are then output (such as to the user as described previously). Once decrypted and decoded, the estimated count for haplotype AB (i.e., $N_{AB}$) can be computed from $\eta$ and $\beta$ such that $N_{AB} = \eta/\beta$. It is noted that $N_{AB}$ is used in calculating the scalar D for linkage disequilibrium as will be described next.

1.1.2.3 Linkage Disequilibrium

Linkage disequilibrium (LD) is an association in the alleles present at each of two sites in a genome (unlike HWE where it is assumed the alleles at each site are independent). Suppose A and a are possible alleles at site 1 and B and b are possible alleles at site 2, and let $p_A$, $p_a$, $p_B$, $p_b$ be their corresponding population frequencies. Similarly, let $p_{AB}$, $p_{Ab}$, $p_{aB}$, $p_{ab}$ be the frequencies of the haplotypes AB, Ab, aB, ab, respectively. Under linkage equilibrium, it is expected these frequencies are independent, ie., it is expected that:

$$p_{AB} = p_A p_B, p_{Ab} = p_A p_b, p_{aB} = p_a p_B, p_{ab} = p_a p_b \tag{45}$$

When the alleles are in linkage disequilibrium (LD), the frequencies will deviate from the values above by a scalar D, so that:

$$p_{AB} = p_A p_B + D, p_{Ab} = p_A p_b - D, N_{aB} = p_a p_B - D, N_{ab} = p_a p_b + D \tag{46}$$

This scalar D is calculated as $D = p_{AB} p_{ab} - p_{Ab} p_{aB} = p_{AB} - p_A p_B$. However, the range of D depends on the frequencies, which makes it difficult to use it as a measure of LD. One of two scaled-down variants is used instead, the D'-measure or the $r^2$-measure.

1.1.2.3.1 D'-Measure

It is easy to show that $\max\{-p_A p_B, -p_a p_b\} \le D \le \min\{p_A p_b, p_a p_B\}$, so that the maximum value $D_{max}$ that $|D|$ can take is:

$$D_{max} = \begin{cases} \min\{p_A p_b, p_a p_B\} & D > 0 \\ \min\{p_A p_B, p_a p_b\} & D < 0 \end{cases} \tag{47}$$

The D'-measure is then defined as $$D' \stackrel{def}{=} \frac{|D|}{D_{max}} \tag{48}$$

The range of D' is [0,1] with a value of 0 meaning complete equilibrium and a value of 1 meaning complete disequilibrium.

1.1.2.3.2 $r^2$-Measure

The $r^2$ measure is given by:

$$r^2 \stackrel{def}{=} \frac{X^2}{N} \tag{49}$$

where $X^2$ is the Pearson Goodness-of-Fit (Chi-Squared) Test statistic:

$$X^2 \stackrel{def}{=} \sum_{i \in \{A,a\}, j \in \{B,b\}} \frac{(O_{ij} - E_{ij})^2}{E_{ij}} \tag{50}$$

where $$O_{ij} \stackrel{def}{=} N_{ij}$$

is the observed count and $$E_{ij} \stackrel{def}{=} N p_i p_j$$

is the expected count. Using the fact that $|O_{ij} - E_{ij}| = ND$, it can be shown that:

$$r^2 = \frac{D^2}{p_A p_B p_a p_b} \tag{51}$$

The range of $r^2$ is [0,1] with a value of 0 meaning perfect equilibrium and a value of 1 meaning perfect disequilibrium.

1.1.2.3.3 Linkage Disequilibrium Using Encrypted Genotype Frequency Counts

In view of the foregoing, LD measurement can be performed using encrypted genotype frequencies as follows. The two vectors of ciphertexts $(\hat{z}_1, \ldots, \hat{z}_K)$, $(\hat{z}'_1, \ldots, \hat{z}'_K)$ encrypting genotype samples in $\{-1, 0, 1, x^\tau\}$, for loci 1 and 2 respectively, and number of iterations m to be performed, are input, along with the ciphertexts $\hat{N}_{00}, \hat{N}_{10}, \hat{N}_{20}, \hat{N}_{01}, \hat{N}_{11}, \hat{N}_{21}, \hat{N}_{02}, \hat{N}_{12}, \hat{N}_{22}$ computed as described previously. Ciphertexts $\hat{\delta}_1, \hat{\delta}_2, \hat{N}_A, \hat{N}_a, \hat{N}_B, \hat{N}_b$ are then computed as follows:

$$\hat{N} \leftarrow \hat{N}_{00} + \hat{N}_{10} + \hat{N}_{20} + \hat{N}_{01} + \hat{N}_{11} + \hat{N}_{21} + \hat{N}_{02} + \hat{N}_{12} + \hat{N}_{22} // \deg(\hat{N}) = 6 \tag{52}$$

$$\hat{R}_0 \leftarrow \hat{N}_{00} + \hat{N}_{01} + \hat{N}_{02}, \hat{R}_1 \leftarrow \hat{N}_{10} + \hat{N}_{11} + \hat{N}_{12}, \hat{R}_2 \leftarrow \hat{N}_{20} + \hat{N}_{21} + \hat{N}_{22} \tag{53}$$

$$\hat{C}_0 \leftarrow \hat{N}_{00}+\hat{N}_{10}+\hat{N}_{20}, \hat{C}_1 \leftarrow \hat{N}_{01}+\hat{N}_{11}+\hat{N}_{21}, \hat{C}_2 \leftarrow \hat{N}_{02}+\hat{N}_{12}+\hat{N}_{22} \quad (54)$$

$$\hat{N}_A \leftarrow 2\hat{R}_0+\hat{R}_1, \hat{N}_a \leftarrow 2\hat{R}_2+\hat{R}_1 // \deg(\hat{N}_A, \hat{N}_a, \hat{N}_B, \hat{N}_b)=6 \quad (55)$$

$$\hat{N}_B \leftarrow 2\hat{C}_0+\hat{C}_1, \hat{N}_b \leftarrow 2\hat{C}_2+\hat{C}_1 \quad (56)$$

$$\hat{\eta}, \hat{\beta} \leftarrow \mathrm{EM}(\hat{z}_1, \ldots, \hat{z}_K \hat{z}'_1, \ldots, \hat{z}'_K, m) // \deg(\hat{\eta})=6 \cdot (2^m-1), \deg(\hat{\beta})=6 \cdot (2^m-2) \quad (57)$$

$$\hat{\delta}_1 \leftarrow 2\hat{N}\hat{\eta}-\hat{N}_A\hat{N}_B\hat{\beta}, \hat{\delta}_2 \leftarrow 2\hat{N}\hat{\beta} // \deg(\hat{\delta}_1, \hat{\delta}_2) \leq 6 \cdot 2^m \quad (58)$$

The ciphertexts $\hat{\delta}_1, \hat{\delta}_2, \hat{N}_A, \hat{N}_a, \hat{N}_B, \hat{N}_b$ are then output (such as to the user as described previously). Once decrypted and decoded, the LD measurement can be computed from $\delta_1, \delta_2, N_A, N_a, N_B, N_b$ such that $D = \delta_1/\delta_2$

1.2 Encoding and Encrypting Phenotypes

In the same way an encoding $E_g$ for genotypes is chosen, an encoding $E_p$ is also chosen for phenotypes. There are two possible phenotypes, 0 and 1, with 0 being the unaffected phenotype and 1 being the affected phenotype. There also may be a missing phenotype, which is represented as -9.

In the case of phenotypes, the encoding can be arbitrarily chosen as $E_p: \{0, 1, -9\} \rightarrow R_q$. To ensure that the coefficients of the encoding (in $R_q$) are small, the following further encoding is employed:

$$E_p(z) \stackrel{def}{=} \begin{cases} -1 & z = 0 \\ 1 & z = 1 \\ 0 & z = -9 \end{cases} \quad (59)$$

For the purposes of the encrypted computations, a 2×3 contingency table of genotype/phenotype counts is needed. To this end, the input is a vector $$\vec{z} \stackrel{def}{=} (z_1, \ldots, z_K)^T \in \{-1, 0, 1, x^\tau\}$$

of genotype samples, and a vector $$\vec{y} \stackrel{def}{=} (y_1, \ldots, y_K)^T \in \{0, 1\}$$

of phenotype samples. For each genotype/phenotype pair $(i,j)$, it is desired to define an indicator polynomial $h_{i,j}$ such that:

$$h_{i,j}(z, y) = \begin{cases} 1 & (z, y) = (E_g(i), E_p(j)) \\ 0 & (z, y) \neq (E_g(i), E_p(j)) \end{cases} \quad (60)$$

Here again, let $(2^{-1})_q$ denote the inverse of 2 modulo q. Lagrange interpolation can be employed to find the polynomial computing each $h_{i,j}$. In one implementation, the following polynomials are computed (over $R_q$):

$$h_{i,1}(z, y) \stackrel{def}{=} g_i(z) \cdot (2^{-1})_q 2 \cdot (y^2 + y) = g_i(z) \cdot g_2(y),$$
$$h_{i,0}(z, y) \stackrel{def}{=} g_i(z) \cdot (2^{-1})_q 2 \cdot (y^2 - y) = g_i(z) \cdot g_0(y) \quad (61)$$

Once the polynomials are computed, the encryption can proceed as described previously.

1.2.1 Counting Genotype/Phenotype Frequencies

The genomic computations also employ genotype/phenotype frequencies.

Given a vector of ciphertexts $(\hat{z}_1, \ldots, \hat{z}_K)$ encrypting genotype samples in $\{-1, 0, 1, x^\tau\}$, and vector of ciphertexts $(\hat{y}_1, \ldots, \hat{y}_K)$ encrypting phenotypes in $\{-1, 1, 0\}$, in one embodiment the genotype/phenotype frequencies are counted using:

$$\hat{N}_{00} \leftarrow \Sigma_{k=1}^K g_0(\hat{z}_k) \cdot g_0(\hat{y}_k), \hat{N}_{10} \leftarrow \Sigma_{k=1}^K g_1(\hat{z}_k) \cdot g_0(\hat{y}_k),$$
$$\hat{N}_{20} \leftarrow \Sigma_{k=1}^K g_2(\hat{z}_k) \cdot g_0(\hat{y}_k)$$

$$\hat{N}_{01} \leftarrow \Sigma_{k=1}^K g_0(\hat{z}_k) \cdot g_2(\hat{y}_k), \hat{N}_{11} \leftarrow \Sigma_{k=1}^K g_1(\hat{z}_k) \cdot g_2(\hat{y}_k),$$
$$\hat{N}_{21} \leftarrow \Sigma_{k=1}^K g_2(\hat{z}_k) \cdot g_2(\hat{y}_k) \quad (62)$$

This produces ciphertexts $\hat{N}_{00}, \hat{N}_{10}, \hat{N}_{20}, \hat{N}_{01}, \hat{N}_{11}, \hat{N}_{21}$ such that $\deg(\hat{N}_{0j}, \hat{N}_{2j})=4$ and $\deg(\hat{N}_{1j})=5$. It is noted that $\hat{N}_{00}$ represents the encrypted genotype/phenotype frequency count of the first homozygous genotype (0)/unaffected phenotype (0), $\hat{N}_{10}$ represents the encrypted genotype/phenotype frequency count of the heterozygous genotype (1)/unaffected phenotype (0), $\hat{N}_{20}$ represents the encrypted genotype/phenotype frequency count of the second homozygous genotype (2)/unaffected phenotype (0), $\hat{N}_{01}$ represents the encrypted genotype/phenotype frequency count of the first homozygous genotype (0)/affected phenotype (1), $\hat{N}_{11}$ represents the encrypted genotype/phenotype frequency count of the heterozygous genotype (1)/affected phenotype (1), and $\hat{N}_{21}$ represents the encrypted genotype/phenotype frequency count of the second homozygous genotype (2)/affected phenotype (1).

Figure 6:
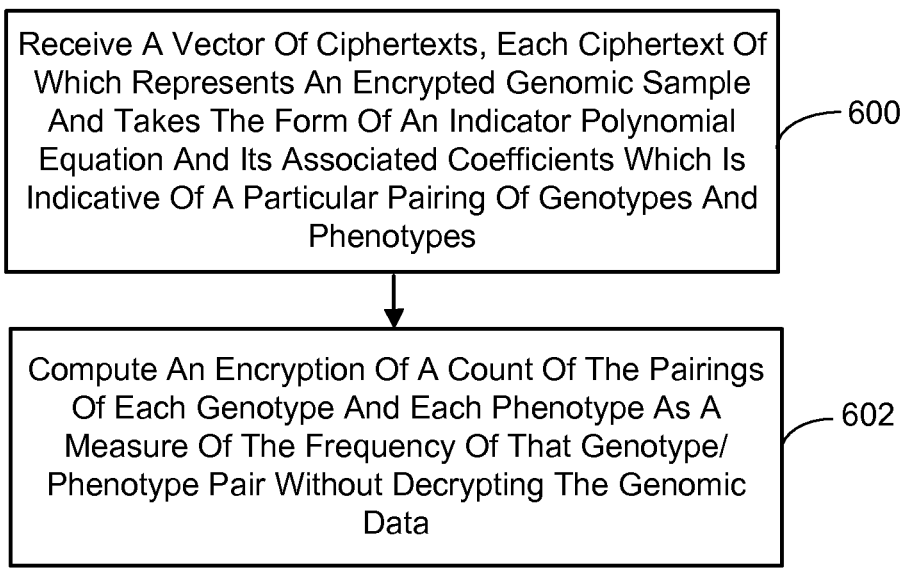
FIG. 6 is a flow diagram generally outlining an implementation of the part of the process of FIG. 3 involving the computation of genotype/phenotype frequency for a single locus.

In procedural terms, referring to FIG. 6, the foregoing genotype/phenotype frequency computation involves first receiving a vector of ciphertexts, each ciphertext of which represents an encrypted genomic sample and takes the form of an indicator polynomial and its associated coefficients which is indicative of a particular pairing of the genotypes and phenotypes (process action 600). Then, an encryption of a count of the pairings of each genotype and each phenotype is computed as a measure of the frequency of that genotype/phenotype pair (process 602). It is noted that this last action is performed without decrypting the genomic data.

1.2.2 Genomic Computations Using Encrypted Genotype and Genotype/Phenotype Frequencies Once the encrypted genotype/phenotype frequencies are computed, various genomic computation can be performed using the encrypted data. For example, the aforementioned Cochran-Armitage test for trend computations can be performed, as will be described in more detail in the sections to follow. It is noted that the definitions described previously also apply to the following descriptions.

1.2.2.1 Cochran-Armitage Test for Trend (CATT)

The Cochran-Armitage test for trend is used for testing association between a candidate allele A and a disease in a case-control study. The input data is a 2×3 contingency table of 3 genotypes vs. case/controls, such as the exemplary table shown in FIG. 7.

The CATT computes the statistic:

$$T \stackrel{def}{=} \sum_{i=1}^{3} w_i(N_{1i}R_2 - N_{2i}R_1) \quad (63)$$

where $$\vec{w} \stackrel{def}{=} (w_1, w_2, w_3)$$

is a vector of pre-determined weights, and the difference $(N_{1i}R_2 - N_{2i}R_1)$ can be thought of as the difference $N_{1i} - N_{2i}$ after reweighing the rows to have the same sum.

The variance of this statistic can be computed as:

$$\text{Var}(T) = \frac{R_1 R_2}{N}\left(\sum_{i=1}^{3} w_i^2 C_i(N - C_i) - 2\sum_{i=1}^{k-1}\sum_{j=i+1}^{k} w_i w_j C_i C_j\right) \quad (64)$$

The test statistic $X^2$ is then defined as follows and compared to a $\chi^2$-statistic with 1 degree of freedom:

$$X^2 \stackrel{def}{=} \frac{T^2}{\text{Var}(T)} \quad (65)$$

As in the Pearson Goodness-of-Fit (Chi-Squared) Test, the p-value p of $X^2$ according to the $\chi^2$-distribution with 1 degree of freedom is computed. It is then concluded that there is no association between the candidate allele and the disease if p>α, for significance level α. When α=0.05, this reduces to checking if $X^2$<3.84; and when α=0.01, this reduces to checking if $X^2$<6.64.

The weights $\vec{w}=(w_1,w_2,w_3)$ are chosen as follows. The weights $\vec{w}=(0,1,2)$ are used for the additive (co-dominant) model, $\vec{w}=(0,1,1)$ for the dominant model (A is dominant over a), and $\vec{w}=(0,0,1)$ for the recessive model (A is recessive to allele a).

1.2.2.2 Cochran-Armitage Test for Trend Using Encrypted Genotype/Phenotypes Frequency Counts In view of the foregoing, CATT can be performed using encrypted genotype/phenotype frequencies as follows. A vector of ciphertexts $(\hat{z}_1, , , \hat{z}_K)$ encrypting genotype samples in $\{-1,0,1,x^\tau\}$, a vector of ciphertexts $(\hat{y}_1, , , \hat{y}_K)$ encrypting phenotypes in $\{-1,0,1\}$, and vector of (plaintext) weights $(w_0,w_1,w_2)$, are input, along with the ciphertexts $\hat{N}_{00},\hat{N}_{10},\hat{N}_{20},\hat{N}_{01},\hat{N}_{11},\hat{N}_{21}$ representing the previously computed encrypted genotype/phenotype frequency counts. Ciphertexts $\hat{\alpha},\hat{\beta}$ are then computed as follows:

$$\hat{R}_0 \leftarrow \hat{N}_{00}+\hat{N}_{10}+\hat{N}_{20}, \hat{R}_1 \leftarrow \hat{N}_{01}+\hat{N}_{11}+\hat{N}_{21}//\deg(\hat{R}_i)=3 \quad (66)$$

$$\hat{C}_0 \leftarrow \hat{N}_{00}+\hat{N}_{01}, \hat{C}_1 \leftarrow \hat{N}_{10}+\hat{N}_{11}, \hat{C}_2 \leftarrow \hat{N}_{20}+\hat{N}_{21}//\deg(\hat{C}_i)=3 \quad (67)$$

$$\hat{N} \leftarrow \hat{R}_0+\hat{R}_1//\deg(\hat{N})=3 \quad (68)$$

$$\hat{T} \leftarrow \Sigma_{i=0}^2 w_i(\hat{N}_{i0}\hat{R}_1 - \hat{N}_{i1}\hat{R}_0)//\deg(\hat{T})=6 \quad (69)$$

$$\hat{\alpha} \leftarrow \hat{N} \cdot \hat{T}^2 //\deg(\hat{\alpha})=15 \quad (70)$$

$$\hat{\beta} \leftarrow \hat{R}_0\hat{R}_1(\Sigma_{i=0}^2 w_i^2 \hat{C}_i(N-\hat{C}_i) - 2\Sigma_{i=0}^1 \Sigma_{j=i+1}^2 w_i w_j \hat{C}_i \hat{C}_j)//\deg(\hat{\beta})=12 \quad (71)$$

Figures 7, 8:
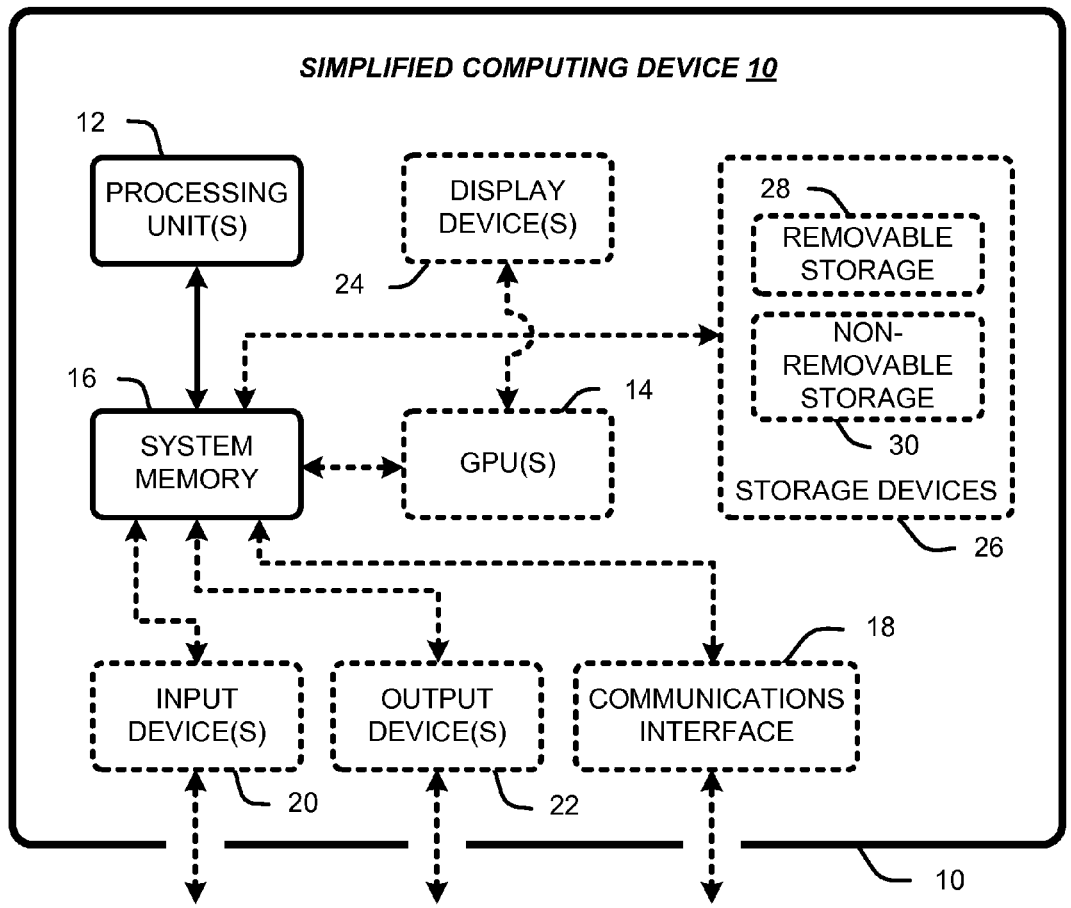
FIG. 7 is an exemplary contingency table of 3 genotypes vs. case/controls.
FIG. 8 is a diagram depicting a general purpose computing device constituting an exemplary system for implementing genomic data encryption embodiments described herein.

The ciphertexts $\hat{\alpha},\hat{\beta}$ are then output (such as to the user as described previously). Once decrypted and decoded, the aforementioned test statistic $X^2$ can be computed from α,β such that $X^2=\alpha/\beta$ 2.0 Exemplary Operating Environments The genomic data encryption embodiments described herein are operational within numerous types of general purpose or special purpose computing system environments or configurations, as indicated previously. FIG. 8 illustrates a simplified example of a general-purpose computer system on which various embodiments and elements of genomic data encryption, as described herein, may be implemented. It is noted that any boxes that are represented by broken or dashed lines in the simplified computing device 10 shown in FIG. 8 represent alternate embodiments of the simplified computing device. As described below, any or all of these alternate embodiments may be used in combination with other alternate embodiments that are described throughout this document. The simplified computing device 10 is typically found in devices having at least some minimum computational capability such as personal computers (PCs), server computers, handheld computing devices, laptop or mobile computers, communications devices such as cell phones and personal digital assistants (PDAs), multiprocessor systems, microprocessor-based systems, set top boxes, programmable consumer electronics, network PCs, minicomputers, mainframe computers, and audio or video media players.

To allow a device to implement the genomic data encryption embodiments described herein, the device should have a sufficient computational capability and system memory to enable basic computational operations. In particular, the computational capability of the simplified computing device 10 shown in FIG. 8 is generally illustrated by one or more processing unit(s) 12, and may also include one or more graphics processing units (GPUs) 14, either or both in communication with system memory 16. Note that that the processing unit(s) 12 of the simplified computing device 10 may be specialized microprocessors (such as a digital signal processor (DSP), a very long instruction word (VLIW) processor, a field-programmable gate array (FPGA), or other micro-controller) or can be conventional central processing units (CPUs) having one or more processing cores.

In addition, the simplified computing device 10 shown in FIG. 8 may also include other components such as a communications interface 18. The simplified computing device 10 may also include one or more conventional computer input devices 20 (e.g., pointing devices, keyboards, audio (e.g., voice) input devices, video input devices, haptic input devices, gesture recognition devices, devices for receiving wired or wireless data transmissions, and the like). The simplified computing device 10 may also include other optional components such as one or more conventional computer output devices 22 (e.g., display device(s) 24, audio output devices, video output devices, devices for transmitting wired or wireless data transmissions, and the like). Note that typical communications interfaces 18, input devices 20, output devices 22, and storage devices 26 for general-purpose computers are well known to those skilled in the art, and will not be described in detail herein.

The simplified computing device 10 shown in FIG. 8 may also include a variety of computer-readable media. Computer-readable media can be any available media that can be accessed by the computer 10 via storage devices 26, and can include both volatile and nonvolatile media that is either removable 28 and/or non-removable 30, for storage of information such as computer-readable or computer-executable instructions, data structures, program modules, or other data. Computer-readable media includes computer storage media and communication media. Computer storage media refers to tangible computer-readable or machine-readable media or storage devices such as digital versatile disks (DVDs), compact discs (CDs), floppy disks, tape drives, hard drives, optical drives, solid state memory devices, random access memory (RAM), read-only memory (ROM), electrically erasable programmable read-only memory (EEPROM), flash memory or other memory technology, magnetic cassettes, magnetic tapes, magnetic disk storage, or other magnetic storage devices.

Retention of information such as computer-readable or computer-executable instructions, data structures, program modules, and the like, can also be accomplished by using any of a variety of the aforementioned communication media (as opposed to computer storage media) to encode one or more modulated data signals or carrier waves, or other transport mechanisms or communications protocols, and can include any wired or wireless information delivery mechanism. Note that the terms "modulated data signal" or "carrier wave" generally refer to a signal that has one or more of its characteristics set or changed in such a manner as to encode information in the signal. For example, communication media can include wired media such as a wired network or direct-wired connection carrying one or more modulated data signals, and wireless media such as acoustic, radio frequency (RF), infrared, laser, and other wireless media for transmitting and/or receiving one or more modulated data signals or carrier waves.

Furthermore, software, programs, and/or computer program products embodying some or all of the various genomic data encryption embodiments described herein, or portions thereof, may be stored, received, transmitted, or read from any desired combination of computer-readable or machine-readable media or storage devices and communication media in the form of computer-executable instructions or other data structures.

Finally, the genomic data encryption embodiments described herein may be further described in the general context of computer-executable instructions, such as program modules, being executed by a computing device. Generally, program modules include routines, programs, objects, components, data structures, and the like, that perform particular tasks or implement particular abstract data types. The data extraction technique embodiments may also be practiced in distributed computing environments where tasks are performed by one or more remote processing devices, or within a cloud of one or more devices, that are linked through one or more communications networks. In a distributed computing environment, program modules may be located in both local and remote computer storage media including media storage devices. Additionally, the aforementioned instructions may be implemented, in part or in whole, as hardware logic circuits, which may or may not include a processor.

3.0 Other Embodiments

The foregoing description of the various genomic data encryption embodiments involved encoding the genomic data before encrypting it. The following describes another encoding embodiment that is designed to encode real numbers, and which can be employed for encoding genomic data.

For a real number $\alpha \in R$, $$decomp(\alpha) \stackrel{def}{=} (\alpha_{k_\alpha}, \, , \, \alpha_0, \alpha_{-1},)$$

is defined to be the (possibly infinite) binary decomposition of $\alpha$, so that:

$$\alpha = \sum_{i=-\infty}^{k_\alpha} \alpha_i 2^i. \tag{72}$$

For a sequence $$\vec{\alpha} \stackrel{def}{=} (\alpha_k, \, , \, \alpha_0, \alpha_{-1}, \, , \alpha_{-s}), \, \text{real}(\vec{\alpha}) \stackrel{def}{=} \sum_{i=-s}^{k} \alpha_i 2^i.$$

The ring $$R \stackrel{def}{=} Z[x]/\langle x^n + 1 \rangle$$

is employed and $\lambda$ is used to denote its expansion factor. For this specific ring, $\lambda = n$.

Now let $\alpha \in R$ be a real number that it is desired to encode as a polynomial in $R = Z[x]/\langle x^n+1 \rangle$, and let u' be the (decimal) precision it is desired to maintain. Let $$F(z) \stackrel{def}{=} \sum_{i=0}^{D} a_i z^i$$

be a degree-D polynomial that can be used in performing computations on the encoded (and encrypted using an appropriate homomorphic encryption scheme) real number data, i.e., it is desired to compute $F(\alpha)$ using decimal precision u'.

Let $decomp(\alpha) = (\alpha_k, \, , \, , \alpha_0, \alpha_{-1},)$. Since it is desired to maintain decimal precision u', binary precision $$u \stackrel{def}{=} 4u' > \log_2(10)u'$$

will be maintained. Therefore only the truncated decomposition $$\vec{\alpha} \stackrel{def}{=} (\alpha_k, \, , \alpha_0, \alpha_{-1}, \, , \alpha_{-u}) \in \{0,1\}^{k+u+1}$$

is considered, so that $$\tilde{\alpha} \stackrel{def}{=} \text{REAL}(\vec{\alpha})$$

approximates $\alpha$ up to decimal precision u'. Computing $$F(\overset{\square}{\alpha})$$

is the only concern.

For i=0,k+u, $$\beta_i \stackrel{def}{=} \alpha_{i-u} \in \{0,1\}$$

is defined and the encoding of $\alpha$ in R is defined as the polynomial:

$$e_\alpha(x) \stackrel{def}{=} \sum_{i=0}^{k+u} \beta_i x^i \in R_2. \tag{73}$$

The idea is then to perform the computation on $e_\alpha$ and decode by evaluating the resulting polynomial at x=2. However, note that $e_\alpha(2)=2^u \cdot \tilde{\alpha}$. Therefore, $$F(\tilde{\alpha}) = F\left(\frac{e_\alpha(2)}{2^u}\right) = \sum_{i=0}^{D} \left(\frac{a_i}{2^{i \cdot u}}\right) e_\alpha(2). \tag{74}$$

Multiplying by $2^{Du}$ results in:

$$2^{Du} \cdot F(\tilde{\alpha}) = \sum_{i=0}^{D} a_i \cdot 2^{(D-i)u} \cdot e_\alpha(2)^i \tag{75}$$

$$= \sum_{i=0}^{D} a_i \cdot x^{(D-i)u} \cdot e_\alpha(x)^i (\bmod(x-2))$$

where the last equality holds as long as there is no reduction modulo $x^n+1$, that is, as long as $Du+D(k+u)=D(2u+\lfloor \log \alpha \rfloor)<n$.

Now define $$G(z) \stackrel{def}{=} \sum_{i=0}^{D} a_i \cdot x^{(D-i)u} \cdot z^i.$$

Then, $$F(\tilde{\alpha}) = \frac{G(e_\alpha)(\bmod(x-2))}{2^{Du}}. \tag{76}$$

This means that to compute $F(\tilde{\alpha})$, simply compute $G(e_\alpha)$, evaluate the resulting polynomial at x=2, and divide by $2^{Du}$. The function G is a transformation of the original function F, and is designed to be used in performing computations on the encoded encrypted real number data. Thus, the encrypted data will be plugged into that function G to carry out the actual computation on encrypted data. The reason for transforming the original function F into G is that the coefficients of the encrypted intermediate results stay smaller. This in turn allows for better parameters and more efficient schemes.

Figure 9:
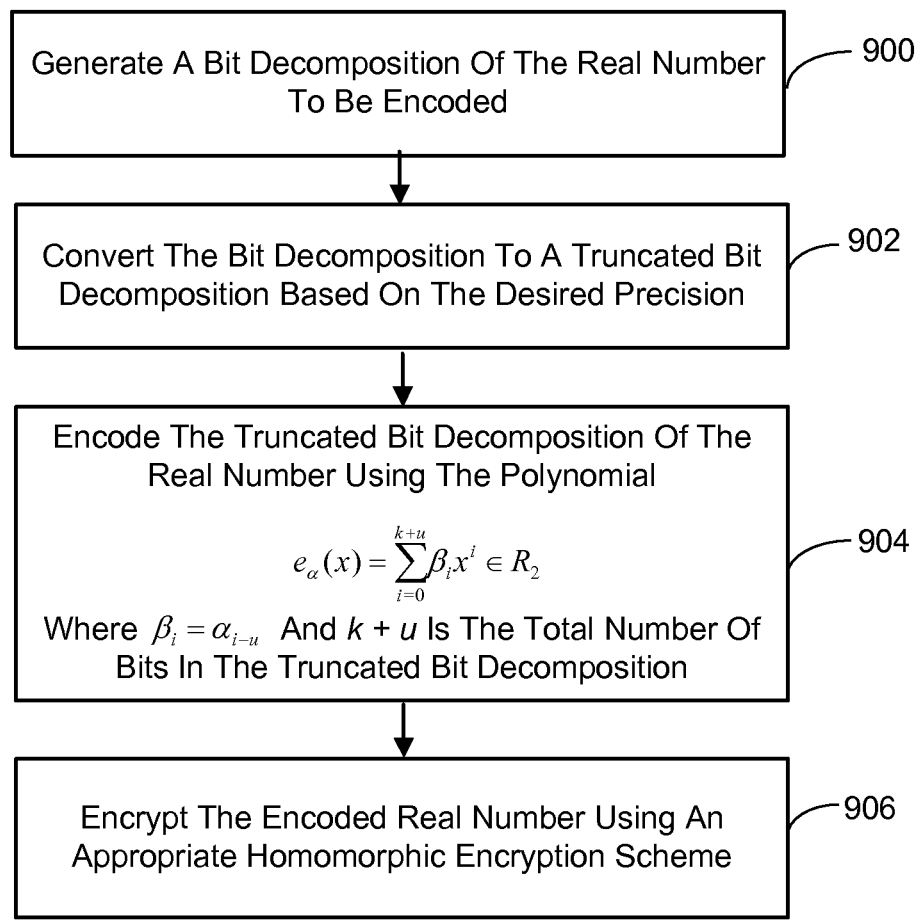
FIG. 9 is a flow diagram generally outlining one embodiment of a process for encrypting real numbers using a homomorphic polynomial encryption scheme.

In procedural terms, referring to FIG. 9, the foregoing homomorphic polynomial encryption scheme for encrypting real numbers involves the encoding and encrypting entity (e.g., the aforementioned user as represented by the user computer) generating a bit decomposition of the real number to be encoded (process action 900). This corresponds to the previously introduced equation $$\text{real}(\tilde{\alpha}) \stackrel{def}{=} \sum_{i=-s}^{k} \alpha_i 2^i$$

for the bit decomposition sequence of the real number $$\vec{\alpha} \stackrel{def}{=} (\alpha_k, , \alpha_0, \alpha_{-1}, \alpha_{-s}).$$

The bit decomposition is then converted to a truncated bit decomposition based on the desired precision (process action 902). Namely, the desired decimal precision u' which corresponds to the binary precision u, as described previously. Thus, as described previously, the truncated bit decomposition $$\vec{\alpha} \stackrel{def}{=} (\alpha_k, , \alpha_0, \alpha_{-1}, , \alpha_{-u})$$

results. The truncated bit decomposition of the real number is then encoded using the polynomial $$e_\alpha(x) = \sum_{i=0}^{k+u} \beta_i x^i \in R_2,$$

where $\beta_i = \alpha_{i-u}$ and k+u is the total number of bits in the truncated bit decomposition (process action 904). Then, in process action 906, the encoded real number is encrypted using an appropriate homomorphic encryption scheme. The encoded and encrypted real number data can then be provided to the entity or entities that perform storage and computations on the data (e.g., the previously described cloud-based entity or entities).

Figure 10:
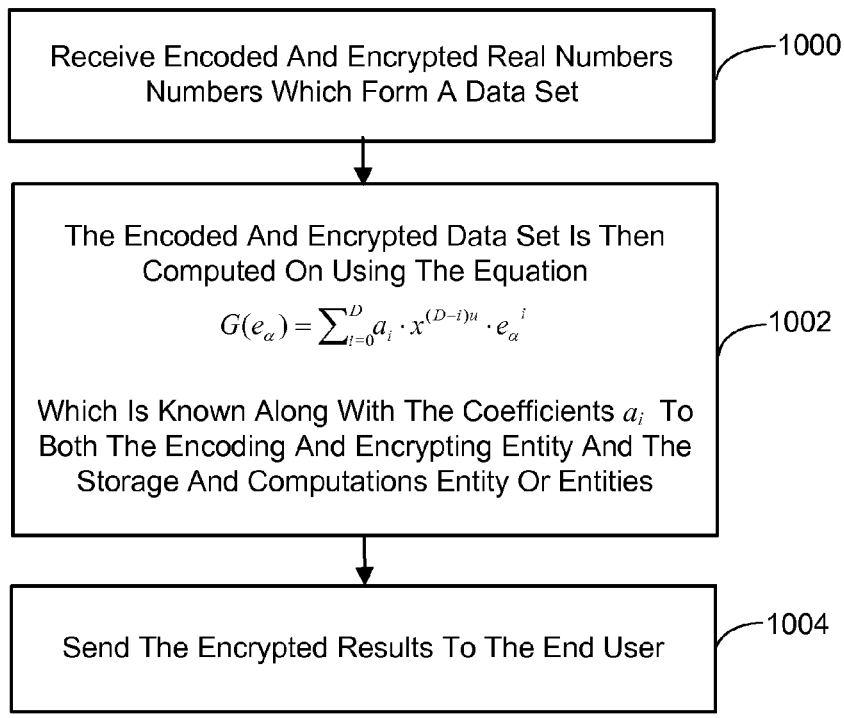
FIG. 10 is a flow diagram generally outlining one embodiment of a process for converting encrypted real numbers to a more noise resistant polynomial form before performing computations on the encrypted numbers, all without first decrypting the numbers.

Referring now to FIG. 10, in process action 1000, the storage and computations entity or entities receive the encoded and encrypted real number, along with other similarly encoded and encrypted real numbers which form a data set (such as the previously described genomic data). The encoded and encrypted data set is then computed on using the equation $G(e_\alpha) = \sum_{i=0}^{D} a_i \cdot x^{(D-i)u} \cdot e_\alpha^i$, which is known along with the coefficients $a_i$ to both the encoding and encrypting entity and the storage and computations entity or entities (process action 1002). It is noted that D is the degree of the polynomial function G (and F). It is also noted that the desired computations (e.g., one or more of the genomic computations described previously) are performed without decrypting the data. In process action 1004 the encrypted results are sent to the end user (e.g., the encrypting entity).

Figure 11:
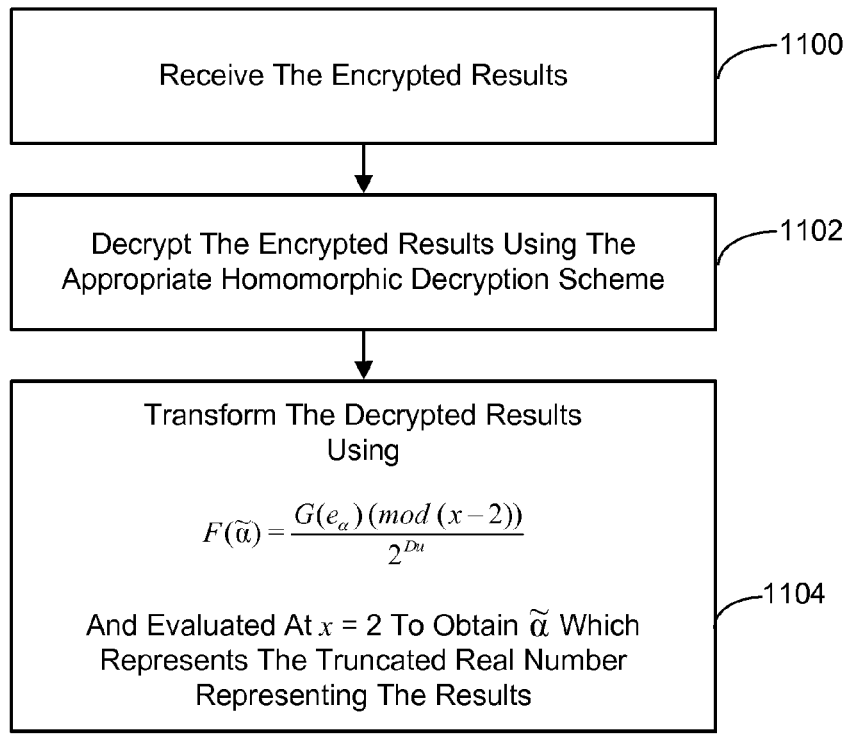
FIG. 11 is a flow diagram generally outlining one embodiment of a process for decrypting the results of computations on encrypted real numbers.

Referring now the FIG. 11, the end user receives the encrypted results (process action 1100), which are in the form of ciphertexts. The encrypted results are first decrypted using the appropriate homomorphic decryption scheme to recover the plaintext polynomials (process action 1102). Then, in process action 1104, the decrypted plaintext polynomials are transformed using Eq. (76) i.e., $$F(\tilde{\alpha}) = \frac{G(e_\alpha)(\bmod(x-2))}{2^{Du}},$$

and evaluated at x=2 to obtain $\tilde{\alpha}$, which represents the truncated real number representing the results.

It is also noted that any or all of the aforementioned embodiments throughout the description may be used in any combination desired to form additional hybrid embodiments. In addition, although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Wherefore, what is claimed is:

1. A computer-implemented process for encrypting genomic data, comprising:
   using a hardware processor of a computer to perform the following process actions:
   receiving genomic data comprising genotypes, said genotypes consisting of a heterozygous genotype, a first homozygous genotype, a second homozygous genotype, and an unknown genotype in the case where the actual genotype is unknown;
   encoding the genomic data as polynomials in a message space of a homomorphic encryption scheme, wherein,
      each of the first homozygous genotypes is represented in the polynomials by an integer −1,
      each of the heterozygous genotypes is represented in the polynomials by an integer 0,
      each of the second homozygous genotypes is represented in the polynomials by an integer 1, and
      each unknown genotype is represented in the polynomials by a function that when encrypted comprises a non-zero polynomial, but which when decrypted produces a zero; and
   encrypting the encoded genomic data using the homomorphic polynomial encryption scheme to produce a vector of ciphertexts, each ciphertext of which represents a different sample of the genomic data and takes the form of a polynomial and its associated coefficients, wherein the encrypted genomic data can be used in genomic computations without having to be decrypted.

2. The process of claim 1, further comprising an action of transmitting the encoded and encrypted genomic data via a computer network for storage and genomic computations.

3. The process of claim 2, further comprising the actions of:
   receiving results of the genomic computations on the encoded and encrypted genomic data, said genomic computations having been performed without decoding and decrypting the data and said results exhibiting the same encoding and encryption as the genomic data;
   decrypting the received results using a homomorphic polynomial decryption scheme applicable to the homomorphic polynomial encryption scheme used to encrypt the encoded genomic data; and
   decoding the decrypted results using a decoding scheme applicable to the encoding scheme used to encode the genomic data.

4. The process of claim 1, wherein the process action of encrypting the encoded genomic data using a homomorphic polynomial encryption scheme to produce a vector of ciphertexts, each ciphertext of which represents a different sample of the genomic data and takes the form of a polynomial and its associated coefficients, comprises an action of forming the polynomial as an indicator polynomial which is indicative of the genotype of the sample.

5. The process of claim 1, wherein the genomic data further comprises phenotypes, said phenotypes consisting of an unaffected phenotype, an affected phenotype, and an unknown phenotype in the case where the actual phenotype is unknown, and wherein the process action of encoding the genomic data, comprises the actions of:
   representing each of the unaffected phenotypes in the polynomials in the message space of the homomorphic encryption scheme by an integer −1;
   representing each of the affected phenotypes in the polynomials in the message space of the homomorphic encryption scheme by an integer 1; and
   representing each unknown phenotype in the polynomials in the message space of the homomorphic encryption scheme by an integer 0.

6. The process of claim 5, wherein the process action of encrypting the encoded genomic data using a homomorphic polynomial encryption scheme to produce a vector of ciphertexts, each ciphertext of which represents a different sample of the genomic data and takes the form of a polynomial and its associated coefficient, comprises an action of forming the polynomial as an indicator polynomial which is indicative of the pairing of the genotype and phenotype of the sample.

7. The process of claim 1, wherein the process action of encrypting the encoded genomic data using a homomorphic polynomial encryption scheme comprises encrypting the encoded genomic data using somewhat homomorphic encryption (SwHE) scheme.

8. A system for performing genomic computations on encrypted genomic data, comprising:
   one or more computing devices, wherein said computing devices are in communication with each other via a computer network whenever there are multiple computing devices; and
   a computer program having program modules executable by one or more hardware processors of the one or more computing devices, the one or more computing devices being directed by the program modules of the computer program to,
      receive the encrypted genomic data, said genomic data having been encrypted using a homomorphic polynomial encryption scheme to produce one or more vectors of ciphertexts, each ciphertext of each vector represents a different sample of the genomic data and takes the form of a polynomial and its associated coefficients, and wherein the genomic data comprising genotypes, said genotypes consisting of a heterozygous genotype, a first homozygous genotype, a second homozygous genotype, and an unknown genotype in the case where the actual genotype is unknown, and
      perform one or more genomic computations on the vector or vectors of ciphertexts of the received said encrypted genomic data without decrypting the genomic data, said genomic computations comprising computing an encryption of a count of each genotype present in each received vector of ciphertexts as a measure of a frequency of that genotype, said count of each genotype being computed without decrypting the genomic data.

9. The system of claim 8, further comprising a program module for transmitting the results of the genomic computations to an end user, said results of the genomic computations exhibiting the same encryption exhibited by the genomic data.

10. The system of claim 9, wherein the end user is the same entity that encrypted the genomic data.

11. The system of claim 9, wherein the end user is a different entity than the entity that encrypted the genomic data, but has been authorized by the encrypting entity to decrypt the results.

12. The system of claim 8, wherein the program module for performing one or more genomic computations on the vector or vectors of ciphertexts received without decrypting the genomic data, further comprises a sub-module for performing a Pearson goodness-of-fit (chi-squared) test to measure data quality using the counts of each genotype.

13. A computer-implemented process for performing computations on data comprising:
   using a hardware processor of a computer to perform the following process actions on the data:
   receiving the data comprising encoded and encrypted real numbers, wherein each encoded and encrypted real number was encoded by generating a bit decomposition of the real number, converting the bit decomposition to a truncated bit decomposition $\vec{\alpha}=(\alpha_k, \,,\,, \alpha_0, \alpha_{-1}, \,,\,, \alpha_{-u})$ based on the desired precision u, encoding the real number using the polynomial $$e_\alpha(x) \stackrel{def}{=} \sum_{i=0}^{k+u} \beta_i x^i \in R_2,$$

where $\beta_i = \alpha_{i-u}$ and k+u is the total number of bits in the truncated bit decomposition and encrypting the encoded real number using a homomorphic encryption scheme;
   performing computations on the encoded and encrypted real numbers without decryption to produce an encrypted results using an equation in the form of $G(e_a) = \sum_{i=0}^{D} a_i \cdot x^{(D-i)u} \cdot e_a^i$, where D is the degree of the polynomial and the $a_i$'s are prescribed coefficients;
   transmitting the encrypted results, wherein each encoded and encrypted real number in the encrypted results can be subsequently decrypted using an homomorphic decryption scheme, and decoded by transforming the decrypted results using $$F(\tilde{\alpha}) = \frac{G(e_\alpha)(\mathrm{mod}(x-2))}{2^{Du}},$$

and evaluated at x=2 to obtain $\tilde{\alpha}$, which represents the truncated real number representing the decoded results.

14. A system for performing genomic computations on encrypted genomic data, comprising:
   one or more computing devices, wherein said computing devices are in communication with each other via a computer network whenever there are multiple computing devices; and
   a computer program having program modules executable by one or more hardware processors of the one or more computing devices, the one or more computing devices being directed by the program modules of the computer program to,
      receive the encrypted genomic data in the form of two vectors of ciphertexts, each vector representing encrypted genotypes from a different locus and each ciphertext of each vector representing an encrypted genotype sample from the locus associated with that vector, wherein the genomic data has been encrypted using a homomorphic polynomial encryption scheme to produce one or more vectors of ciphertexts, each ciphertext of which represents a different sample of the genomic data and takes the form of a polynomial and its associated coefficients, and wherein the genomic data comprising genotypes, said genotypes consisting of a heterozygous genotype, a first homozygous genotype, a second homozygous genotype, and an unknown genotype in the case where the actual genotype is unknown, and
      perform one or more genomic computations on the vectors of ciphertexts of the received said encrypted genomic data without decrypting the genomic data, said genomic computations comprising computing an encryption of a count of the pairings of each genotype from one of the vectors with each genotype from the other vector as a measure of a frequency of that genotype pair, said count of each genotype paring being computed without decrypting the genomic data.

15. The system of claim 14, wherein the program module for performing one or more genomic computations on the or vectors of ciphertexts received without decrypting the genomic data, further comprises a sub-module for performing an estimation maximization for haplotyping to estimate haplotype frequencies from the genotype pairing counts.

16. The system of claim 14, wherein the program module for performing one or more genomic computations on the vector Of vectors of ciphertexts received without decrypting the genomic data, further comprises a sub-module for performing a linkage disequilibrium measurement to estimate correlation between genes from the genotype pairing counts.

17. A system for performing genomic computations on encrypted genomic data, comprising:
   one or more computing devices, wherein said computing devices are in communication with each other via a computer network whenever there are multiple computing devices; and
   a computer program having program modules executable by one or more hardware processors of the one or more computing devices, the one or more computing devices being directed by the program modules of the computer program to,
      receive the encrypted genomic data in the form of a vector of ciphertexts, each ciphertext of which represents an encrypted genomic sample and takes the form of an indicator polynomial and its associated coefficients which is indicative of the pairing of the genotype and phenotype of the sample, said genomic data having been encrypted using a homomorphic polynomial encryption scheme to produce said vector of ciphertexts, and wherein the genomic data comprising genotypes, said genotypes consisting of a heterozygous genotype, a first homozygous genotype, a second homozygous genotype, and an unknown genotype in the case where the actual genotype is unknown, and wherein the genomic data further comprises phenotypes, said phenotypes consisting of an unaffected phenotype, an affected phenotype, and an unknown phenotype in the case where the actual phenotype is unknown, and
      perform one or more genomic computations on the vector of ciphertexts of the received said encrypted genomic data without decrypting the genomic data, said genomic computations comprising computing an encryption of a count of the pairings of each genotype and each phenotype as a measure of a frequency of that genotype/phenotype pair, said count of each genotype/phenotype paring being computed without decrypting the genomic data.

18. The system of claim 17, wherein the program module for performing one or more genomic computations on the vector of ciphertexts received without decrypting the genomic data, further comprises a sub-module for performing a Cochran-Armitage test for trends on the correlations between genotypes and phenotypes from the genotype/phenotype pairing counts.

* * * * *